US010543024B2

(12) United States Patent
Lee et al.

(10) Patent No.: US 10,543,024 B2
(45) Date of Patent: Jan. 28, 2020

(54) ADJUSTABLE SPINE DISTRACTION IMPLANT

(71) Applicant: Life Spine, Inc., Huntley, IL (US)

(72) Inventors: David Lee, Hattiesburg, MS (US); James Payne, Vancleave, MS (US)

(73) Assignee: LIFE SPINE, INC., Huntley, IL (US)

(*) Notice: Subject to any disclaimer, the term of this patent is extended or adjusted under 35 U.S.C. 154(b) by 201 days.

(21) Appl. No.: 15/200,459

(22) Filed: Jul. 1, 2016

(65) Prior Publication Data

US 2017/0027618 A1 Feb. 2, 2017

Related U.S. Application Data

(63) Continuation of application No. 13/562,037, filed on Jul. 30, 2012, now Pat. No. 9,381,050, which is a continuation of application No. 12/100,718, filed on Apr. 10, 2008, now Pat. No. 8,231,656.

(60) Provisional application No. 60/911,003, filed on Apr. 10, 2007.

(51) Int. Cl.
*A61B 17/70* (2006.01)

(52) U.S. Cl.
CPC ...... *A61B 17/7067* (2013.01); *A61B 17/7068* (2013.01); *A61B 17/7083* (2013.01)

(58) Field of Classification Search
CPC .......................................... A61B 17/7062–707
See application file for complete search history.

(56) References Cited

U.S. PATENT DOCUMENTS

| | | | |
|---|---|---|---|
| 4,466,426 A | 8/1984 | Blackman | |
| 4,636,217 A | 1/1987 | Ogilvie et al. | |
| 5,390,683 A | 2/1995 | Pisharodi | |
| 5,645,599 A | 7/1997 | Samani | |
| 5,658,335 A | 8/1997 | Allen | |
| 5,658,337 A | 8/1997 | Kohrs et al. | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A * | 5/2000 | Zucherman .......... | A61B 17/025 606/249 |
| 6,074,390 A | 6/2000 | Zucherman et al. | |

(Continued)

FOREIGN PATENT DOCUMENTS

| | | |
|---|---|---|
| KR | 20050119791 | 12/2005 |
| WO | WO-2006/102485 | 9/2006 |

(Continued)

OTHER PUBLICATIONS

"Bacfuse® Spinous Process Fusion Plate Surgical Technique", © 2011, Pioneer Surgical, 12 pages.

(Continued)

*Primary Examiner* — Jacqueline T Johanas
(74) *Attorney, Agent, or Firm* — Foley & Lardner LLP

(57) ABSTRACT

An adjustable spine distraction implant alleviates pain associated with spinal stenosis and facet arthropathy by expanding the volume and/or cross sectional area in the spinal canal and/or neural foramen. The adjustable implant provides a spinal extension inhibitor. The implant includes elliptical or oval shaped adjustable member or spacer for positioning between and adjustably spacing apart the spinous processes.

17 Claims, 14 Drawing Sheets

(56) References Cited

U.S. PATENT DOCUMENTS

| | | | | |
|---|---|---|---|---|
| 6,126,660 | A | 10/2000 | Dietz | |
| 6,126,689 | A | 10/2000 | Brett | |
| 6,176,882 | B1 | 1/2001 | Biedermann et al. | |
| 6,183,471 | B1 | 2/2001 | Zucherman et al. | |
| 6,190,387 | B1 | 2/2001 | Zucherman et al. | |
| 6,235,030 | B1 * | 5/2001 | Zucherman | A61B 17/7062 606/249 |
| 6,375,682 | B1 | 4/2002 | Fleischmann et al. | |
| 6,409,766 | B1 | 6/2002 | Brett | |
| 6,451,019 | B1 | 9/2002 | Zucherman et al. | |
| 6,491,724 | B1 | 12/2002 | Ferree | |
| 6,494,883 | B1 | 12/2002 | Ferree | |
| 6,537,320 | B1 | 3/2003 | Michelson | |
| 6,648,917 | B2 | 11/2003 | Gerbec et al. | |
| 6,695,842 | B2 * | 2/2004 | Zucherman | A61B 17/7068 606/249 |
| 6,699,246 | B2 | 3/2004 | Zucherman et al. | |
| 6,699,247 | B2 | 3/2004 | Zucherman et al. | |
| 6,723,126 | B1 | 4/2004 | Berry | |
| 6,773,460 | B2 | 8/2004 | Jackson | |
| 6,796,983 | B1 | 9/2004 | Zucherman et al. | |
| 6,902,566 | B2 * | 6/2005 | Zucherman | A61B 17/7068 606/60 |
| 6,953,477 | B2 | 10/2005 | Berry | |
| 7,018,415 | B1 | 3/2006 | McKay | |
| 7,048,736 | B2 | 5/2006 | Robinson et al. | |
| 7,087,055 | B2 | 8/2006 | Lim et al. | |
| 7,101,375 | B2 * | 9/2006 | Zucherman | A61B 17/7065 606/249 |
| 7,306,628 | B2 * | 12/2007 | Zucherman | A61B 17/7065 623/17.11 |
| 7,695,513 | B2 | 4/2010 | Zucherman et al. | |
| 7,731,751 | B2 | 6/2010 | Butler et al. | |
| 7,749,252 | B2 * | 7/2010 | Zucherman | A61B 17/7068 606/248 |
| 8,048,117 | B2 * | 11/2011 | Zucherman | A61B 17/7068 606/248 |
| 8,097,019 | B2 | 1/2012 | Mitchell et al. | |
| 8,231,656 | B2 | 7/2012 | Lee et al. | |
| 8,241,330 | B2 | 8/2012 | Lamborne et al. | |
| 8,287,569 | B1 | 10/2012 | Powell | |
| 8,343,190 | B1 | 1/2013 | Mueller et al. | |
| 8,382,801 | B2 | 2/2013 | Lamborne et al. | |
| 8,409,286 | B2 | 4/2013 | McKay | |
| 8,500,778 | B2 * | 8/2013 | Jackson | A61B 17/7062 606/249 |
| 8,574,300 | B2 | 11/2013 | McManus et al. | |
| 8,603,142 | B2 | 12/2013 | Robinson | |
| 2001/0012938 | A1 * | 8/2001 | Zucherman | A61B 17/7065 606/249 |
| 2002/0128716 | A1 | 9/2002 | Cohen et al. | |
| 2003/0040746 | A1 | 2/2003 | Mitchell et al. | |
| 2003/0216736 | A1 * | 11/2003 | Robinson | A61B 17/7068 606/86 B |
| 2003/0236520 | A1 | 12/2003 | Lim et al. | |
| 2004/0153156 | A1 | 8/2004 | Cohen et al. | |
| 2004/0167625 | A1 | 8/2004 | Beyar et al. | |
| 2004/0172134 | A1 | 9/2004 | Berry | |
| 2004/0193159 | A1 * | 9/2004 | Zucherman | A61B 17/7068 606/279 |
| 2005/0033437 | A1 | 2/2005 | Bao et al. | |
| 2005/0049590 | A1 | 3/2005 | Alleyne et al. | |
| 2005/0131536 | A1 | 6/2005 | Eisermann et al. | |
| 2005/0143827 | A1 | 6/2005 | Globerman et al. | |
| 2005/0165398 | A1 * | 7/2005 | Reiley | A61B 17/025 606/86 A |
| 2005/0196420 | A1 * | 9/2005 | Zucherman | A61B 17/7053 424/423 |
| 2005/0222681 | A1 | 10/2005 | Richley et al. | |
| 2005/0228391 | A1 | 10/2005 | Levy et al. | |
| 2005/0261769 | A1 | 11/2005 | Moskowitz et al. | |
| 2005/0278036 | A1 | 12/2005 | Leonard et al. | |
| 2006/0004447 | A1 * | 1/2006 | Mastrorio | A61B 17/7065 623/17.11 |
| 2006/0036258 | A1 | 2/2006 | Zucherman et al. | |
| 2006/0064166 | A1 * | 3/2006 | Zucherman | A61B 17/7065 623/17.11 |
| 2006/0084988 | A1 | 4/2006 | Kim | |
| 2006/0089718 | A1 * | 4/2006 | Zucherman | A61B 17/7065 623/17.11 |
| 2006/0095136 | A1 | 5/2006 | McLuen | |
| 2006/0149385 | A1 | 7/2006 | McKay | |
| 2006/0189999 | A1 | 8/2006 | Zwirkoski | |
| 2006/0235521 | A1 * | 10/2006 | Zucherman | A61B 17/025 623/17.11 |
| 2006/0241601 | A1 | 10/2006 | Trautwein et al. | |
| 2006/0241643 | A1 * | 10/2006 | Lim | A61B 17/025 606/90 |
| 2006/0241770 | A1 | 10/2006 | Rhoda et al. | |
| 2006/0264938 | A1 | 11/2006 | Zucherman et al. | |
| 2007/0142915 | A1 | 6/2007 | Altarac et al. | |
| 2007/0233098 | A1 * | 10/2007 | Mastrorio | A61B 17/7065 606/86 A |
| 2007/0255415 | A1 | 11/2007 | Edie et al. | |
| 2007/0270812 | A1 | 11/2007 | Peckham | |
| 2008/0108990 | A1 * | 5/2008 | Mitchell | A61B 17/7065 606/305 |
| 2008/0114455 | A1 * | 5/2008 | Lange | A61B 17/7062 623/17.16 |
| 2008/0114456 | A1 | 5/2008 | Dewey et al. | |
| 2008/0140207 | A1 | 6/2008 | Olmos et al. | |
| 2008/0161818 | A1 * | 7/2008 | Kloss | A61B 17/025 606/90 |
| 2008/0177391 | A1 | 7/2008 | Mitchell et al. | |
| 2008/0183211 | A1 | 7/2008 | Lamborne et al. | |
| 2008/0256716 | A1 | 10/2008 | Wahrmund et al. | |
| 2008/0312741 | A1 | 12/2008 | Lee et al. | |
| 2009/0062915 | A1 | 3/2009 | Kohm et al. | |
| 2010/0241167 | A1 | 9/2010 | Taber et al. | |
| 2011/0022090 | A1 | 1/2011 | Gordon et al. | |
| 2011/0066186 | A1 | 3/2011 | Boyer et al. | |
| 2011/0144692 | A1 | 6/2011 | Saladin et al. | |
| 2011/0166600 | A1 | 7/2011 | Lamborne et al. | |
| 2011/0172709 | A1 | 7/2011 | Lyons et al. | |
| 2011/0172711 | A1 | 7/2011 | Kirschman | |
| 2011/0184468 | A1 | 7/2011 | Metcalf et al. | |
| 2011/0224731 | A1 | 9/2011 | Smisson et al. | |
| 2012/0016418 | A1 | 1/2012 | Chin et al. | |
| 2012/0059474 | A1 | 3/2012 | Weiman | |
| 2012/0109203 | A1 | 5/2012 | Dryer et al. | |
| 2012/0143252 | A1 | 6/2012 | Robinson | |
| 2012/0221051 | A1 | 8/2012 | Robinson | |
| 2012/0253395 | A1 | 10/2012 | Linares | |
| 2012/0265204 | A1 | 10/2012 | Schmierer et al. | |
| 2012/0296378 | A1 | 11/2012 | Lee et al. | |
| 2013/0079880 | A1 | 3/2013 | Wolters et al. | |
| 2014/0194991 | A1 | 7/2014 | Jimenez | |

FOREIGN PATENT DOCUMENTS

| | | |
|---|---|---|
| WO | WO 2006/105437 | 10/2006 |
| WO | WO-2006/110578 | 10/2006 |
| WO | WO-2007/121070 | 10/2007 |
| WO | WO-2009/124269 | 10/2009 |
| WO | WO-2011/019758 | 2/2011 |

OTHER PUBLICATIONS

Communication and Search Report for European Application No. 12836814.9, dated Oct. 7, 2015, 10 pages.

International Search Report and Written Opinion for International Application No. PCT/US2012/057324, dated Dec. 20, 2012, 10 pages.

* cited by examiner

FIG. 3
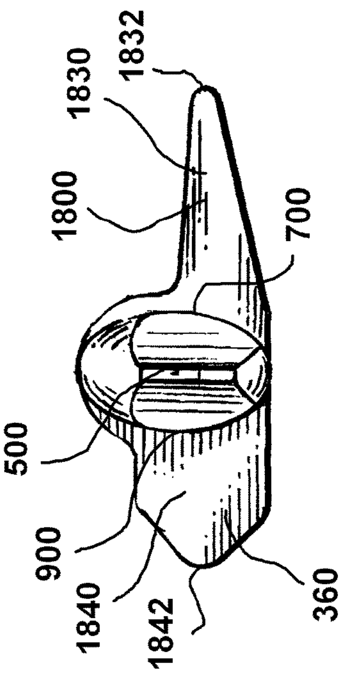
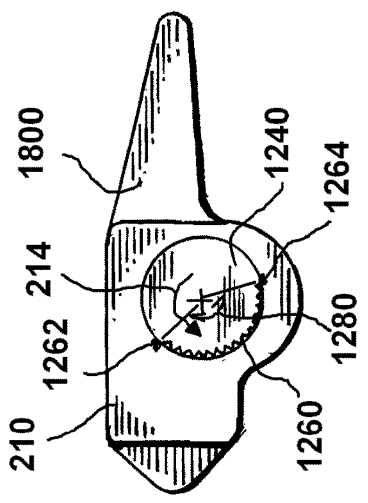
FIG. 4
FIG. 5
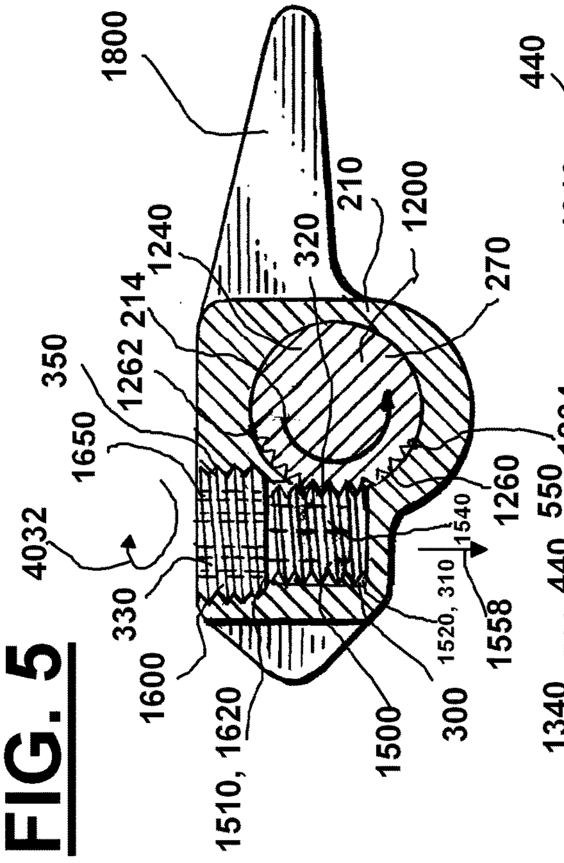
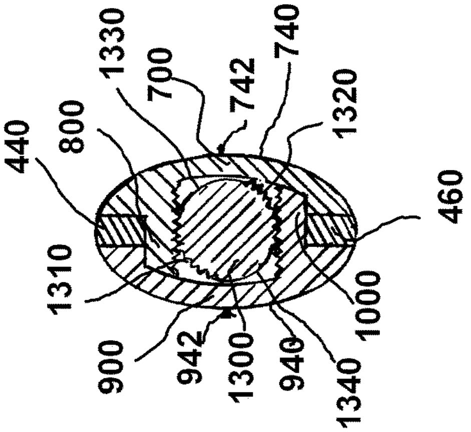
FIG. 6
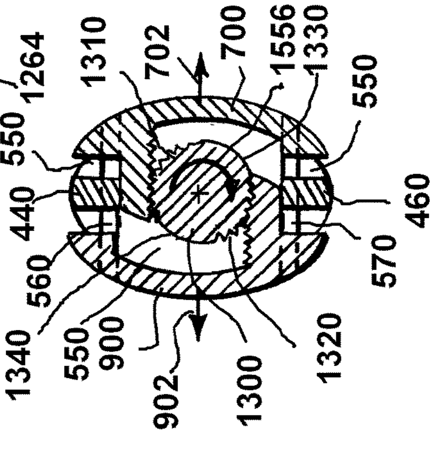
FIG. 7

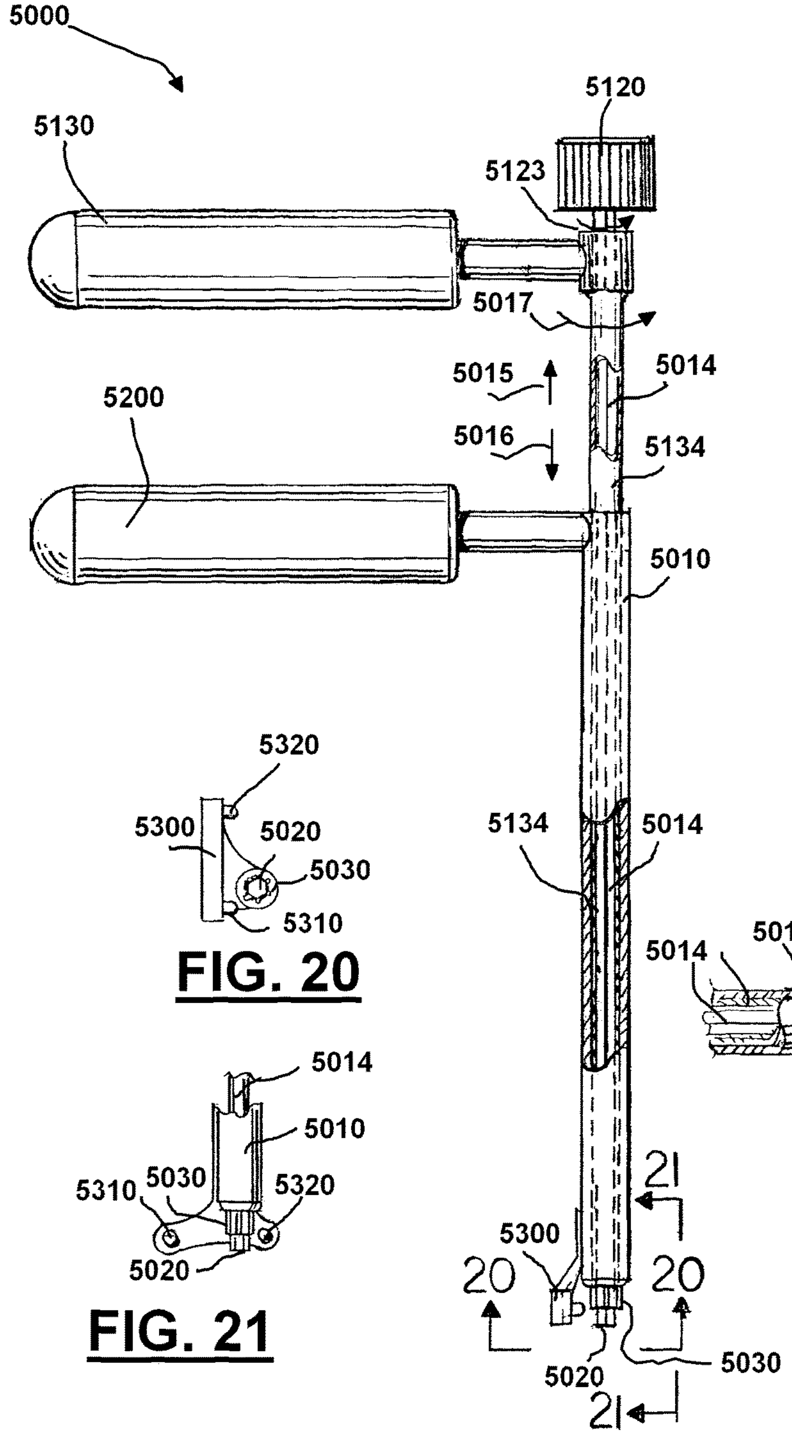
FIG. 20
FIG. 21
FIG. 19
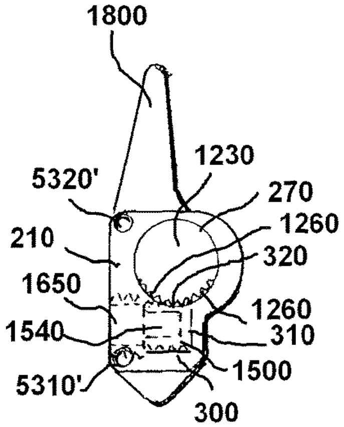
FIG. 22
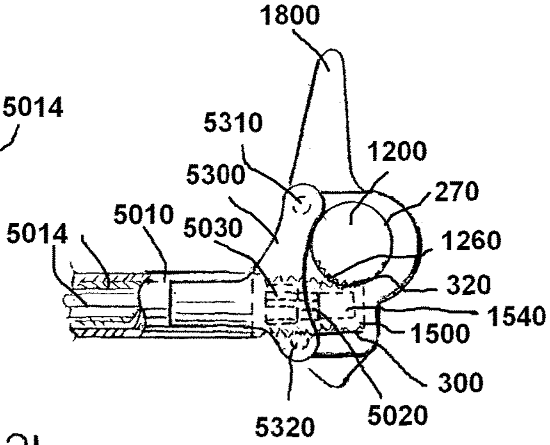
FIG. 23

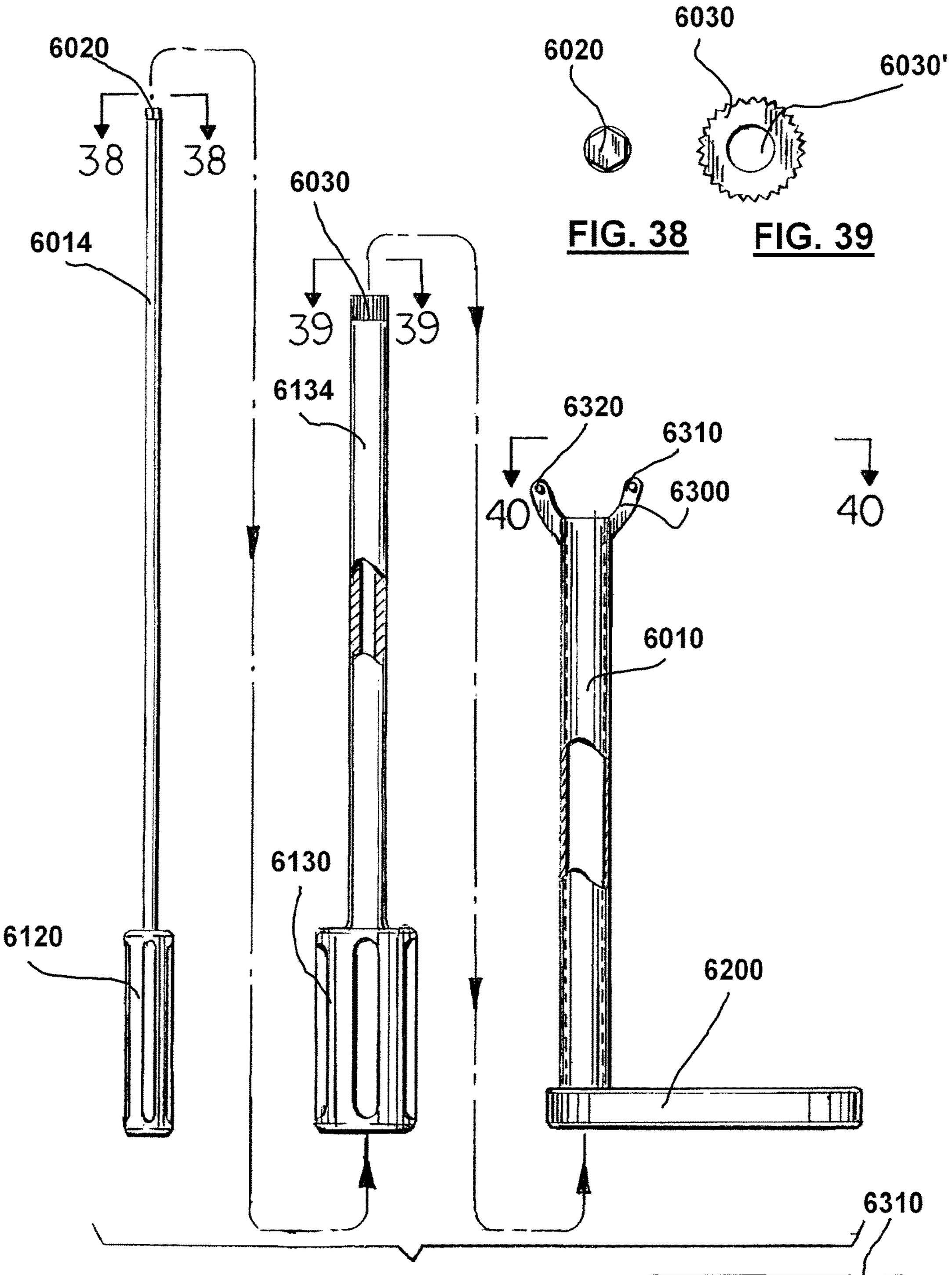
FIG. 38
FIG. 39
FIG. 37
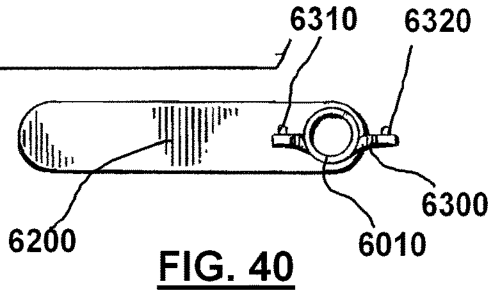
FIG. 40

ADJUSTABLE SPINE DISTRACTION IMPLANT

CROSS-REFERENCE TO RELATED APPLICATIONS

This application is a continuation of application Ser. No. 13/562,037, filed Jul. 30, 2012, which is a continuation of application Ser. No. 12/100,718, filed Apr. 10, 2008, which claims the benefit of Provisional Application No. 60/911, 003, filed Apr. 10, 2007. The entire disclosures of all of these applications are hereby incorporated by reference herein.

BACKGROUND

The spine includes a row of 26 bones in the back and allows a person to stand up straight and bend over. The spine also protects a perso5n's spinal cord from being injured. In people with spinal stenosis, the spine is narrowed in one or more of three parts: (1) the space at the center of the spine; (2) the canals where nerves branch out from the spine; and (3) the space between vertebrae (the bones of the spine). This narrowing puts pressure on the spinal cord and nerves and can cause pain.

Caused by aging spinal stenosis is most common in men and women over 50 years old. Younger people who were born with a narrow spinal canal or who hurt their spines may also get spinal stenosis. Changes that occur in the spine as people get older are the most common cause of spinal stenosis such as: (a) the bands of tissue that support the spine may get thick and hard; (b) bones and joints may get bigger; and (c) surfaces of the bones may bulge out, which are called bone spurs.

In some cases arthritis, a degenerative condition, can cause spinal stenosis. Two forms of arthritis that may affect the spine are: (a) osteoarthritis and (b) rheumatoid arthritis.

Osteoarthritis is the most common form of arthritis and most often occurs in middle aged and older people. It may involve many joints in the body where it wears away the tough tissue (cartilage) that keeps the joints in place and can cause bone spurs and problems with joints.

Rheumatoid Arthritis affects most people at a younger age than osteoarthritis. It causes the soft tissues of the joints to swell and can affect internal organs and systems. However, it is not a common cause of spinal stenosis but can cause severe damage, especially to joints.

Some people are born with conditions that cause spinal stenosis. For instance, some people are born with a small spinal canal. Others are born with a curved spine (scoliosis). Other causes of spinal stenosis are: tumors of the spine; injuries; Paget's disease (a disease that affects the bones); too much fluoride in the body; and calcium deposits on the ligaments that run along the spine.

In many cases there may be no symptoms of spinal stenosis, or symptoms may appear slowly and get worse over time. Signs of spinal stenosis include: pain in the neck or back; numbness, weakness, cramping, or pain in the arms or legs; pain going down the leg; and foot problems.

One type of spinal stenosis, cauda equine syndrome, is very serious. This type occurs when there is pressure on nerves in the lower back. Symptoms may include: loss of control of the bowel or bladder; problems having sex; and pain, weakness, or loss of feeling in one or both legs.

Because spinal stenosis has many causes and symptoms, treatment may be required from doctors who specialize in certain aspects of the condition. Health care providers can include: rheumatologists (doctors who treat arthritis and related disorders); neurologists and neurosurgeons (doctors who treat diseases of the nervous system); orthopedic surgeons (doctors who treat problems with the bones, joints, and ligaments); and physical therapists.

As people age the amount of adverse spinal conditions tend to increase. For example, increases in spinal stenosis, such as central canal and lateral stenosis, along with the thickening of the bones making up the spinal column and facet arthropathy are expected. Spinal stenosis typically includes a reduction in the available space for the passage of blood vessels and nerves which can impinge on these. Pain associated with such stenosis can be relieved by surgery. However, it is desirable to reduce the circumstances for which major surgeries are required to address stenosis.

Accordingly, it is desired to develop procedures and implants for surgically addressing stenosis through minimally invasive procedures, and preferably such surgical procedures can be performed on an outpatient basis.

U.S. Pat. No. 7,101,375 is incorporated herein by reference.

SUMMARY

One embodiment provides a minimally invasive adjustable implant and method for alleviating discomfort associated with the spinal column.

One embodiment provides a method and apparatus for relieving pain by relieving the pressure and restrictions on the blood vessels and nerves associated with the spine. This can be accomplished using an adjustable implant and method which distracts the spinous process of adjacent vertebra in order to alleviate the problems caused by spinal stenosis, facet arthropathy, and similar conditions.

One embodiment provides an adjustable implant for relieving pain comprising an adjustable device positioned between a first spinous process and a second spinous process. The adjustable device includes a vertebra expander or distractor.

One embodiment provides an adjustable implant which is positioned between a first spinous process and a second spinous process, and includes at least one expandable distraction wedge or plate that can adjustably distract the first and second spinous processes as the implant is positioned between the spinous processes as the wedging is expanded and/or retracted. In one embodiment two expandable wedging members are provided which can expand in substantially opposite directions.

One embodiment provides an adjustable implant adapted for increasing the volume and/or cross sectional area of the spinal canal and/or the neural foramen as the implant is positioned between adjacent spinous processes.

One embodiment provides a method for relieving pain due to conditions such as spinal stenosis and facet arthropathy. The method includes the steps of accessing adjacent first and second spinal processes of the spinal column and using an adjustable implant to distract these processes a sufficient amount in order to increase the volume and/or cross sectional area of the spinal canal and relieve pain.

One embodiment provides a method and apparatus which includes implanting an adjustable device which can be adjusted in order to achieve a desired amount of distraction and also maintain such distraction.

One embodiment provides an adjustable implant including a first portion and a second portion. The portions can be expanded and/or retracted in order to achieve the desired amount of distraction.

One embodiment provides an adjustable implant which includes an adjustable body. The adjustable central body can include first and second portions which can be expanded and/or retracted in order to achieve the desired amount of distraction.

One embodiment provides an adjustable implant which includes a first unit having an adjustable central body with a first wing at the first end of the unit. The adjustable implant can includes a guide extending from a second end of the unit and spaced apart from the first wing. The adjustable implant can further include a second wing which can be detachably connectable to the first unit, wherein the adjustable central body is located between the first and second wings.

One embodiment provides an adjustable implant with adjustable body having first and second wings, wherein at least one of the first and second wings is also adjustable relative to the other wing to accommodate spinous processes of different sizes.

One embodiment includes an implant with an adjustable body to be able to accommodate the anatomical structure of multiple spinous processes and different sizes of spinous processes.

One embodiment includes an adjustable implant with an adjustable body, the adjustable body having an elliptical cross section. In other embodiments the cross section can be circular, polygonal, square, rectangular, trapezoidal, quadralateral, etc. In other embodiments the cross section can be symmetric. In other embodiments the cross section can non-symmetric, such as one shape of one side of the cross section and another shape on the other side of the cross section. For example, the cross section can have a half elliptical cross section on one side and a rectangular cross section on the other side. In other embodiments various permutations of the above specified shapes can be on each side of the cross section.

Various embodiments of the method and apparatus can be used to increase the volume and/or cross sectional area of the spinal canal thereby alleviating restrictions on vessels and nerves associated therewith, and reducing pain caused by such restrictions.

While certain novel features of this invention shown and described below are pointed out in the annexed claims, the invention is not intended to be limited to the details specified, since a person of ordinary skill in the relevant art will understand that various omissions, modifications, substitutions and/or changes in the forms and details of the device illustrated and in its operation may be made without departing in any way from the spirit of the present invention. No feature of the invention is critical or essential unless it is expressly stated as being "critical" or "essential."

BRIEF DESCRIPTION OF THE DRAWINGS

FIG. 3 is an end view of the body portion, taken along lines 3-3 of FIG. 1;

FIG. 4 is an end view of the body portion, taken along lines 4-4 of FIG. 1;

FIG. 5 is a sectional view of the body portion taken along the lines 5-5 of FIG. 1;

FIG. 6 is a sectional view of the body portion taken along the lines 6-6 of FIG. 1;

FIG. 7 is a partial sectional view of the body portion in an expanded position;

FIG. 19 is an elevation view of an adjusting tool;

FIG. 20 is a fragmentary view of the adjusting tool taken along lines 20-20 of FIG. 19;

FIG. 21 is a fragmentary view of the adjusting tool taken along lines 21-21 of FIG. 19;

FIG. 22 is a side view of the body;

FIG. 23 is a side view of the body with adjusting tool engaged;

FIG. 37 is a side view showing the three pieces of wing adjustment tool.

FIG. 38 is a bottom view of the wing adjustment tool taken from the lines 38-38 of FIG. 37.

FIG. 39 is a bottom view of the wing adjustment tool taken from the lines 39-39 of FIG. 37.

FIG. 40 is a top view of the wing adjustment tool of FIG. 37.

DESCRIPTION OF EXEMPLARY EMBODIMENTS

Figure 16:
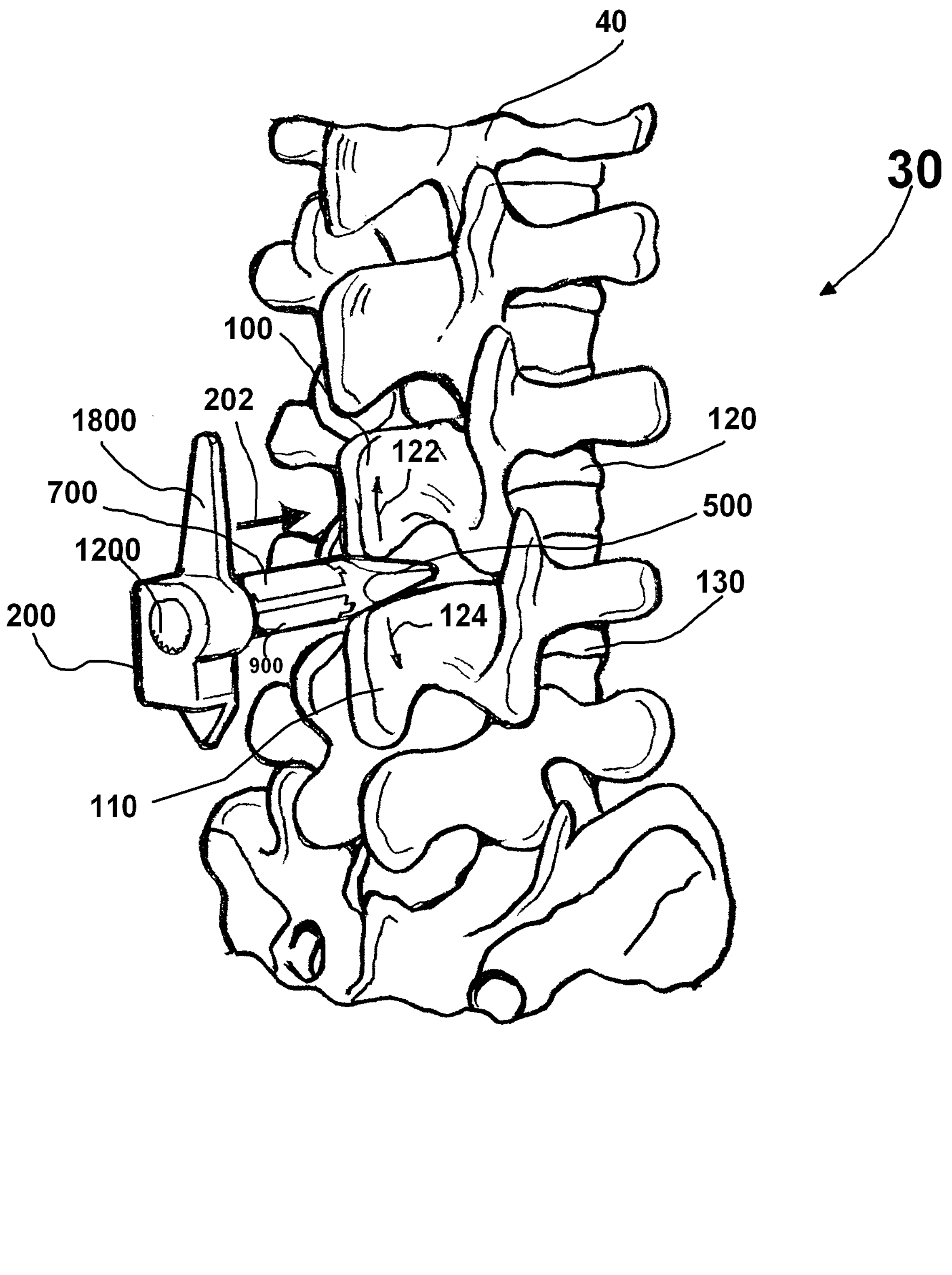
FIG. 16 is a perspective, partially exploded view of the preferred embodiment of the apparatus of the present invention illustrating implantation.
Figure 17:
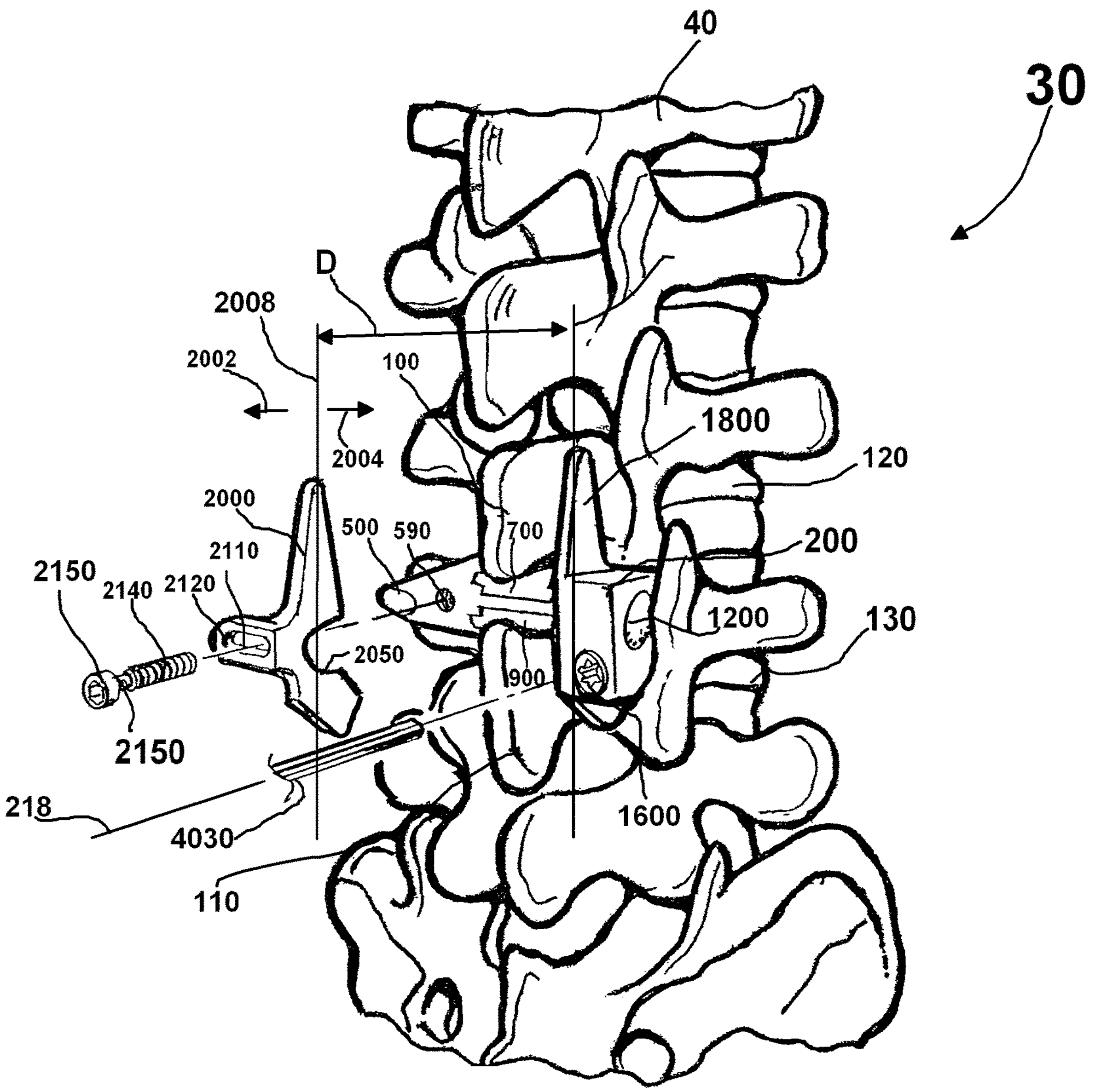
FIG. 17 is a perspective view of the preferred embodiment of the apparatus of the present invention illustrating implantation.
Figure 18:
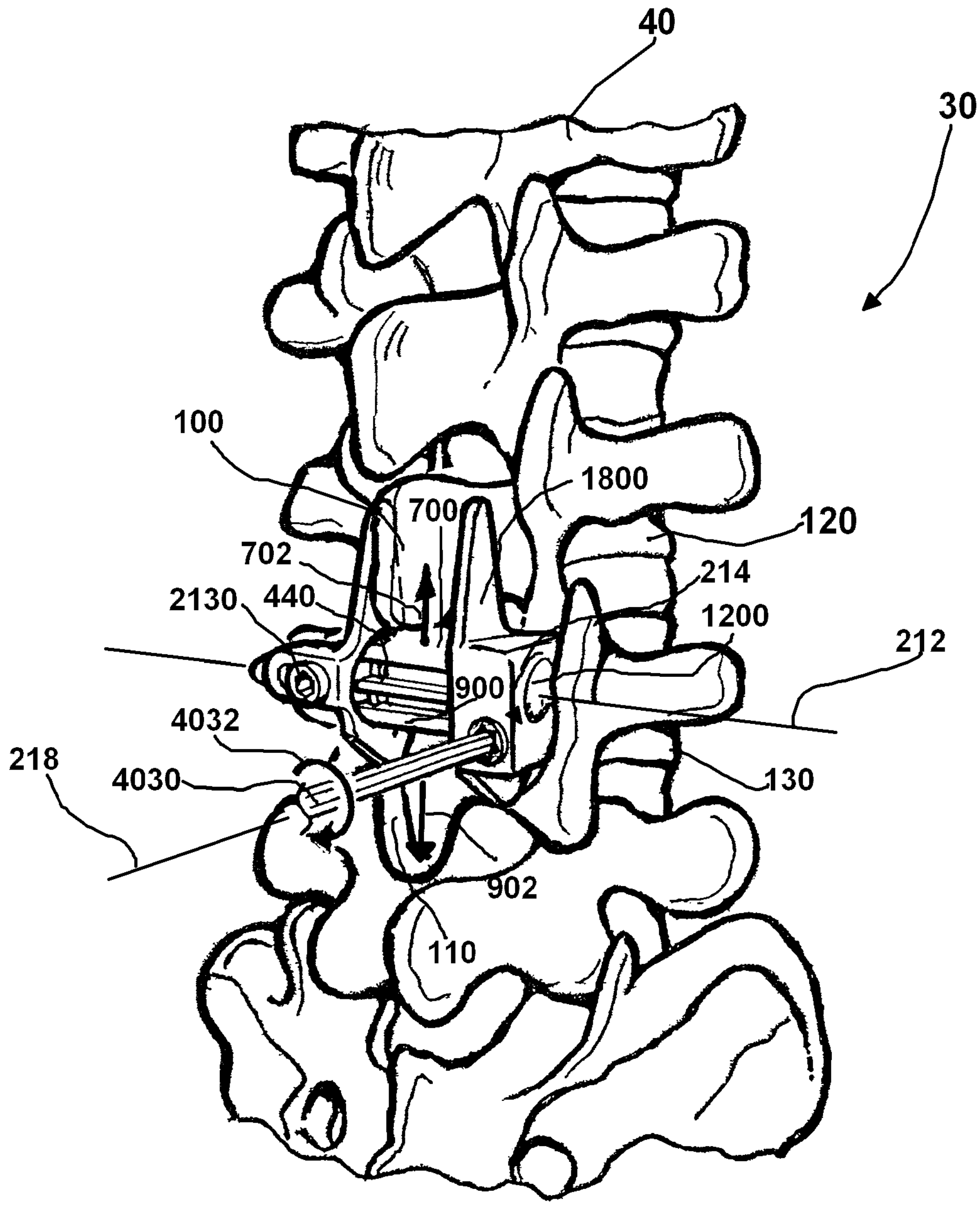
FIG. 18 is a perspective view of the preferred embodiment of the apparatus of the present invention illustrating implantation.
Figure 24:
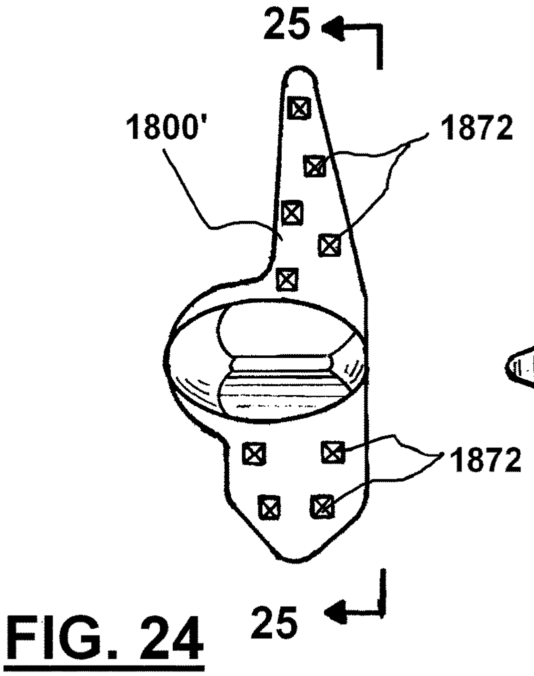
FIG. 24 is an end view of a second embodiment of the apparatus of the present invention.
Figure 25:
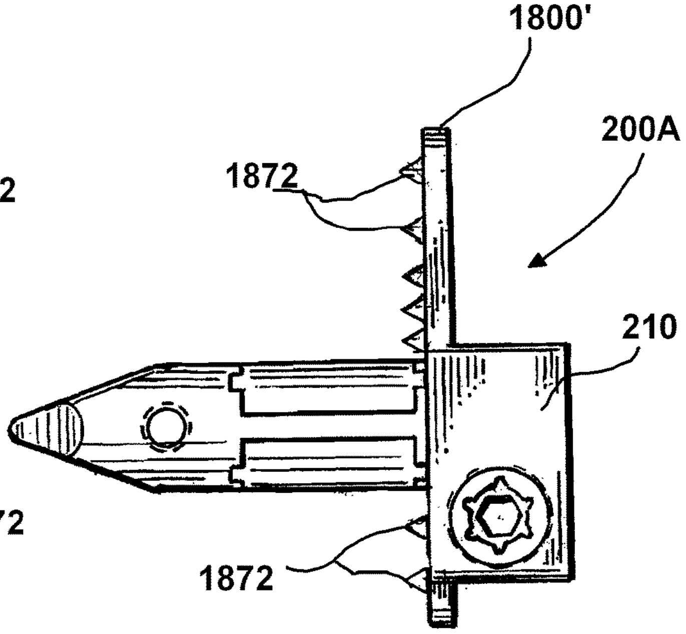
FIG. 25 is a side taken along lines 25-25 of FIG. 24.
Figure 26:
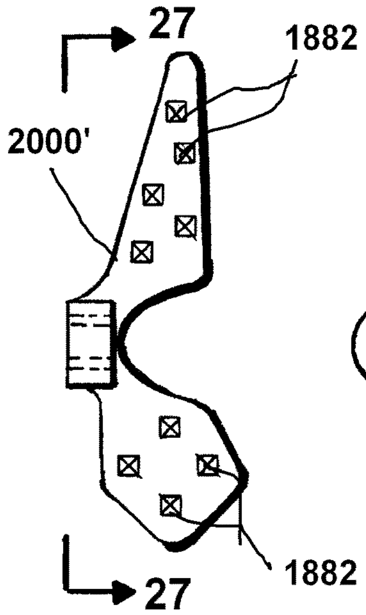
FIG. 26 is a side view of a fixture or wing part of the second embodiment of the apparatus of the present invention.
Figure 27:
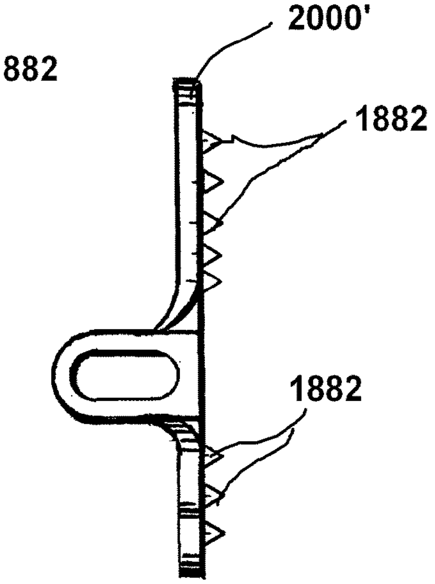
FIG. 27 is a side view taken along lines 27-27 of FIG. 26.

FIGS. 16 through 18 are perspective views of a portion of a spinal column 30. Spinal column 30 includes a plurality of vertebrae 40 with spinous processes (e.g., 100 and 110). Spinal column 30 also includes the spinal cord and nerve roots (not shown for clarity). In one embodiment the apparatus can be implanted to increase the volume and/or cross sectional area of spinal canal thereby alleviating restrictions on vessels and nerves 60 associated therewith, and reducing pain caused by such restrictions.

For purposes of implantation between adjacent first and second spinous processes 100 and 110 of spinal column 30 (see FIGS. 16 through 18), adjustable implant 200 can be configured as shown in FIGS. 1 through 43. First and second spinous processes 100 and 110 are exposed using appropriate surgical techniques and thereafter, adjustable implant 200 is positioned so that upper wedging member 700 engages first spinous process 100, and lower wedging member 900 engages second spinous process 110 (e.g., see FIG. 15,18). At this point, wedging members 700, 900 can be caused to expand respectively in the directions of arrows 702 and 902 (e.g., see FIG. 18) by manipulation of control screw 1500 with tool 4030. Such expansion spreads apart or distracts spinous processes 100 and 110 with the beneficial effect of enlarging the volume and/or cross sectional area of the spinal canal in order to alleviate restrictions on blood vessels and nerves.

Figure 1:
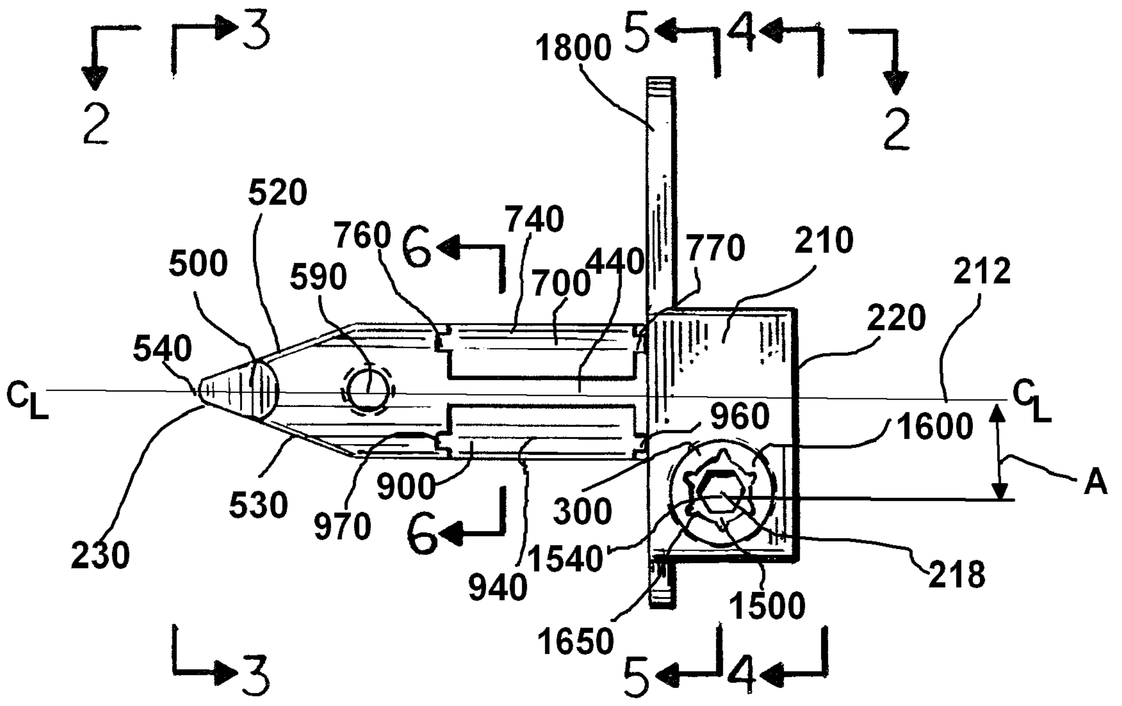
FIG. 1 is an elevation view of the preferred embodiment of the apparatus of the present invention.
Figure 2:
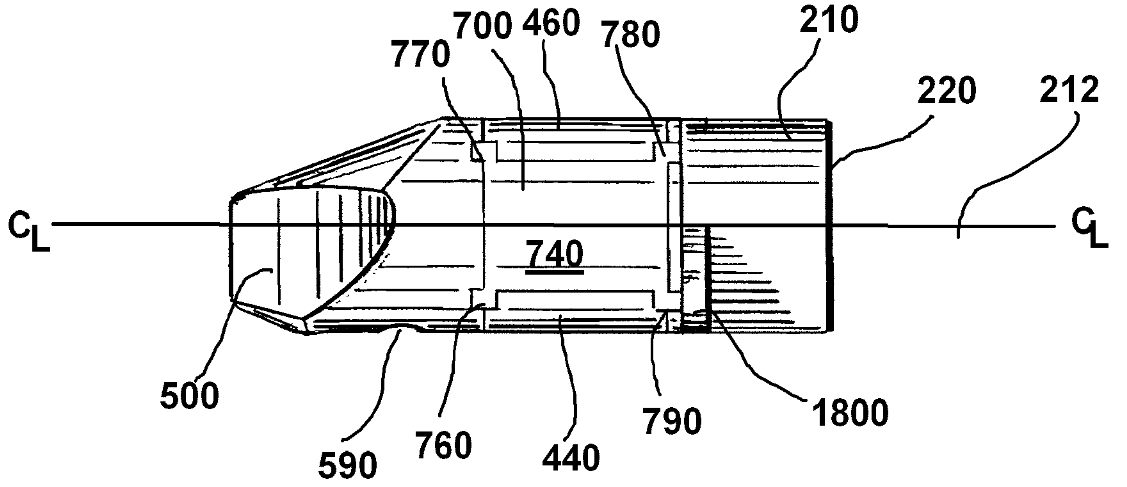
FIG. 2 is a top view of the preferred embodiment of the apparatus of the present invention showing the body portion of an adjustable implant, taken along lines 2-2 of FIG. 1.

Generally, adjustable implant can comprise body 210 along with first and second wedging members 700 and 900 (see, e.g., FIG. 1). First and second wedging members can be mechanically expanded in the respective directions (and retracted in the opposite directions) of arrows 702 and 902. As will be described below first and second wedging members 700 and 900 can be operatively connected to adjusting screw or worm gear 1200. In one embodiment, when adjusting screw 1200 is turned in a first direction (e.g., in the direction of arrow 214 in FIG. 4, and in the direction of arrow 1556 in FIG. 7) wedging members 700 and 900 expand or move respectively in the directions of arrows 702 and 902. When adjusting screw 1200 is turned in the opposite direction (i.e., in the opposite direction of arrow 214 in FIG. 4 and arrow 1556 in FIG. 7) wedging members 700 and 900 retract or move respectively in the opposite directions of arrows 702 and 902. For both expansion and retraction, a controlled change in the state of expansion or retraction can be obtained through the use of a worm gear on adjusting screw 1200.

Figure 15:
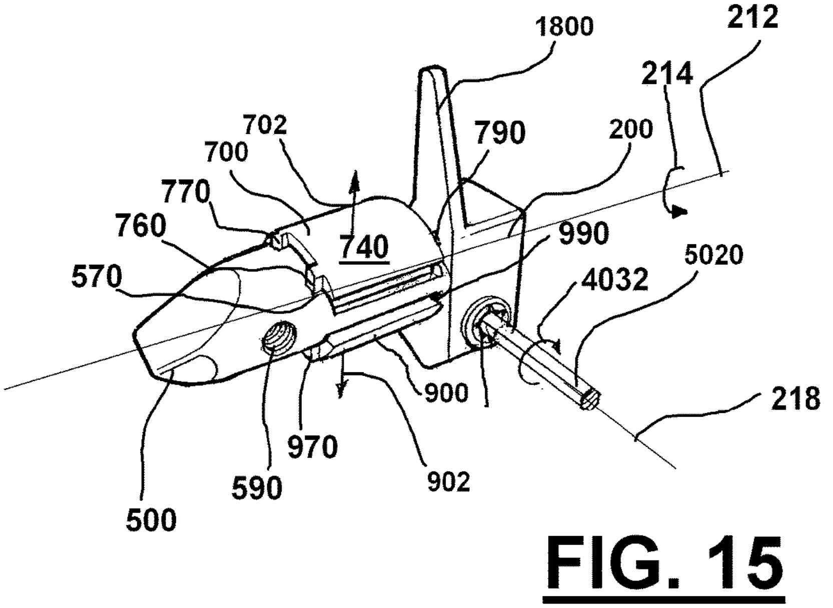
FIG. 15 is a partial perspective view of the preferred embodiment of the apparatus of the present invention showing adjusting of the control.

In FIGS. 7 and 15, an expanded position of wedging members 700 and 900 is shown. In FIGS. 1, 2, 6, 11, and 14 a retracted or collapsed position of wedging members 700, 900 can be seen. The amount of expansion (or contraction) of wedging members 700 and 900 can be controlled by adjusting screw 1200 and control screw 1500. In one embodiment a control screw 1500 can be operatively connected to adjusting member 1200 such as by a worm gear connection. Control screw 1500 can be placed in bore 300 of body 210 (e.g., FIG. 5 where bore 300 is not threaded) and operatively connected to gear teeth or threads 1260 of adjusting screw 1200 through opening 320 of body 210. As control screw 1500 is turned in the direction of arrow 4032 (see FIG. 5), adjusting screw 1200 will move in the direction of arrow 214. On the other hand, as control screw 1500 is turned in the opposite direction of arrow 4032 (see FIG. 5), adjusting screw 1200 will move in the opposite direction of arrow 214. Turning of adjusting screw 1200 causes wedging members 700 and 900 to move: (a) respectively in the directions of arrows 702 and 900 or (b) respectively in the opposite directions of arrows 702 and 902, each case depending on the rotative direction of adjusting screw 1200 or gear.

By controlling the expansion or retraction of wedging members 700 and 900, a surgeon can control the amount of distraction caused by wedging members 700 and 900 upon a pair of spinous processes where adjustable implant 200 is placed in between. Such control can allow a surgeon to use a single adjustable implant 200 to properly distract spinous processes 100 and 110 of multiple sizes and configurations (see e.g., FIGS. 16-18). In prior art devices, such controlled amount of distraction is not available and spinous processes 100 and 110 of different sizes or configurations require multiple sizes of distraction implants.

With prior art distraction implants the surgeon may not be able to tell the proper size of the prior art distraction implants required for a particular set of spinous processes 100 and 110, and will select a first prior art implant of a first size and attempt to implant same and realize that the desired amount of distraction is not obtained (because the selected prior art implant is too small) or that too much distraction is obtained (because the selected prior art implant is too large). If the distraction amount is too small the surgeon will have to remove the selected prior art implant and select a different prior art implant (of larger size) hoping that this second implant will provide an appropriate amount of distraction. This slows down the implantation process and unnecessarily aggravates the tissue and bony area around spinous processes 100 and 110. If the distraction amount is too large (beyond having to implant a second implant) damage may actually occur from excessive distraction.

FIGS. 1-15 show more particularly the construction of adjustable spine distraction implant 200. A body/housing 210 provides first 220 and second 230 end portions. A gear case or body 210 has a dual diameter socket that includes large internally threaded bore 330 and smaller non-threaded bore 300. Bore 300 is receptive of control screw 1200. Bore 330 is receptive of threaded locking screw or nut 1600. As shown in FIG. 5, the locking screw 1600 on the upper end, and base 310 on the lower end limits the amount of vertical movement (schematically indicated by arrow 1558 of FIG. 5) of control screw 1500 thus allowing control screw 1500 to rotate adjusting screw or gear 1200 and finally expand or retract wedging members 700 and 900.

Figure 8:
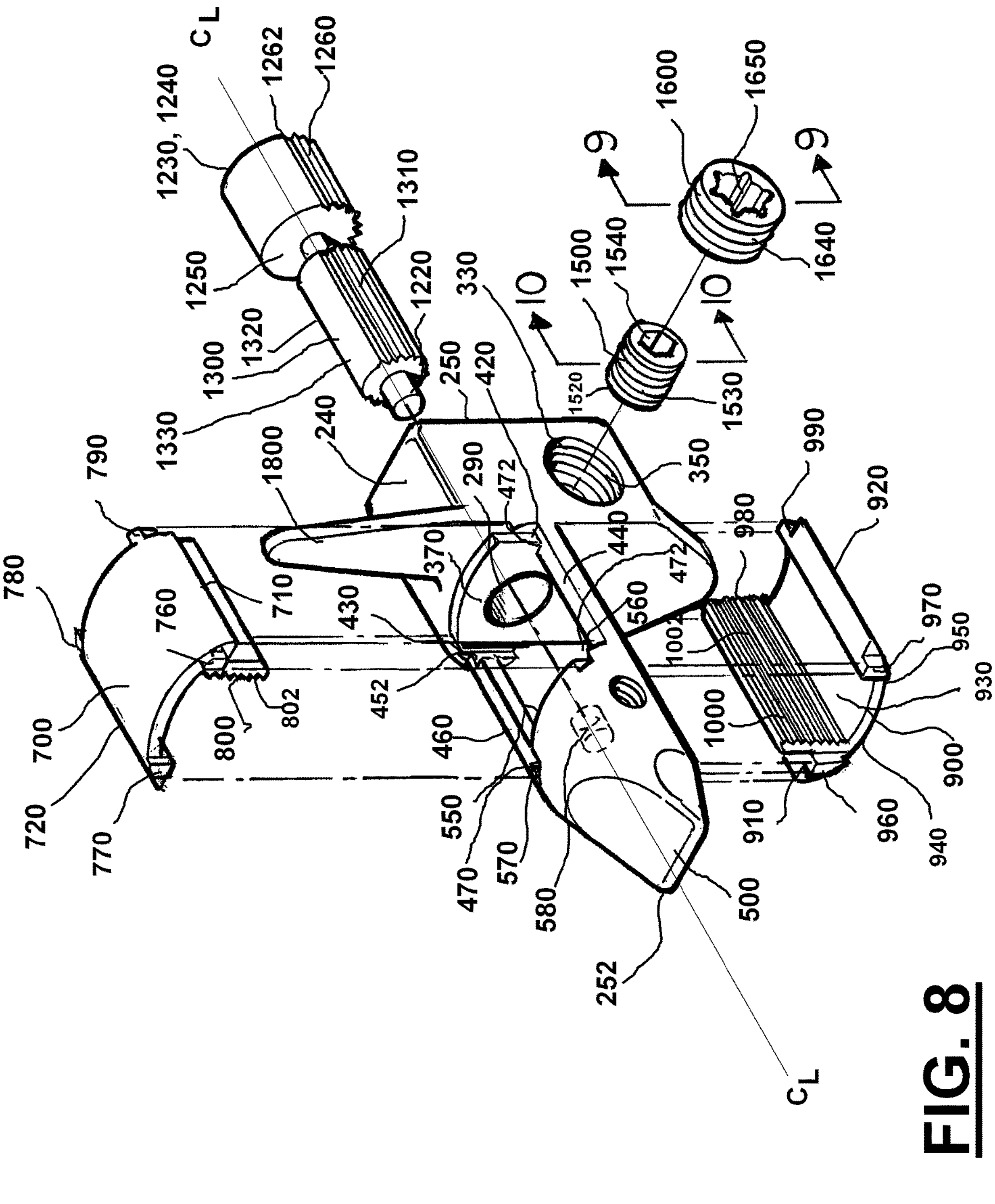
FIG. 8 is a perspective exploded view of the preferred embodiment of the apparatus of the present invention.
Figure 9:
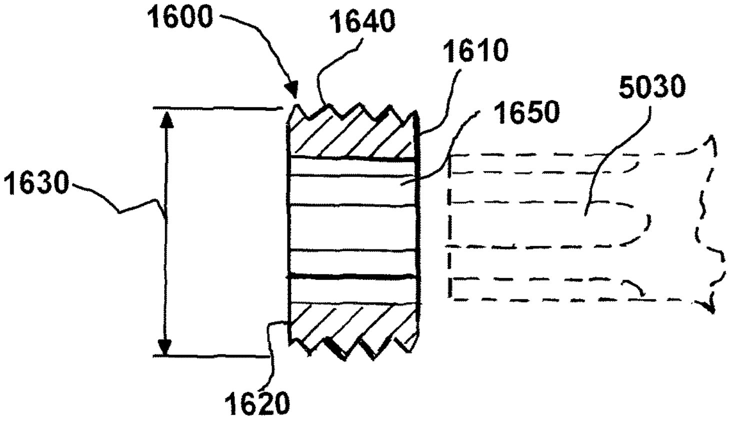
FIG. 9 is a fragmentary sectional view of the preferred embodiment of the apparatus of the present invention showing the threaded cap.
Figure 10:
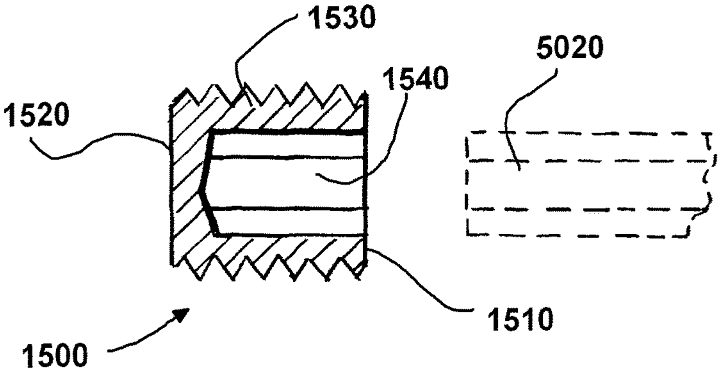
FIG. 10 is a sectional view of the adjusting screw.

As shown in FIGS. 8 and 10, control screw 1500 can have a tool (e.g. allen wrench) receptive socket 1540 that is receptive of a tool end 5020 and external thread 1530. The tool end portion 5020 of tool 5120 interlocks with socket 1540 (e.g. allen wrench receptive) of threaded control screw 1500. As shown in FIGS. 8 and 9, locking screw or nut 1600 can have a tool (e.g. star) receptive socket 1650 that connects with tool 5030. The tool end portion 5030 interconnects with socket (e.g. star drive) 1650 of locking screw or nut 1600. Locking screw or nut 1600 can have external threads 1640.

Tool 5020 can be used to turn control screw 1500 which in turn rotates adjusting screw 1200 which in turn expands or retracts wedging members 700 and 900. Tool 5030 can be used to frictionally lock control screw in place and prevent further movement of adjusting screw 1200 or wedging members 700 and 900.

After locking screw or nut 1600 is loosened, second tool or driver 5020 can be used to rotate control screw 1500 and thus rotate adjusting screw or gear 1200 in a selected direction (such as that indicated by arrow 214 in FIG. 5, or in the opposite direction of arrow 214). As shown in FIGS. 4, 5, and 8, adjusting screw or gear 1200 can be rotatively connected to body 210 through first longitudinal bore 270 and longitudinal bore 580. Second end 1220 of adjusting screw or gear 1200 is supported by and rotates in longitudinal bore 580 while head 1230 rotates in and is supported by first longitudinal bore 270.

FIGS. 5 and 8 shows one embodiment of adjusting screw 1200 being operably connected to wedging members 700 and 900, and how control screw 1500 can be operably connected to adjusting screw 1200 thereby making control screw 1500 operably connected to wedging members 700 and 900. FIG. 6 is a schematic view of adjustable implant 200 where wedging members 700 and 900 are in a retracted state. FIG. 7 is a schematic view showing wedging members 700 and 900 in a partially to completely extended or expanded state.

FIGS. 4, 6, 7, and 18 schematically show that, as adjusting screw 1200 rotates in the direction of arrow 214 (or from the opposite view in the direction of arrow 1556 shown in FIG. 7), wedging members 700 and 900 respectively move in the directions of arrows 702 and 902. Similarly, if rotation is in the opposite direction of arrow 214 (or in the opposite direction of arrow 1556 in FIG. 7), wedging members 700 and 900 move respectively in the opposite directions of arrows 702 and 902. As shown in FIGS. 6 through 8, middle section 1300 of adjusting screw or gear 1200 can be operatively connected to arm 800 of wedging member 700 through threaded or gear toothed area 1310 cooperating with threaded arm 800. Middle section 1300 of adjusting screw or gear 1200 can be operatively connected to arm 1000 of wedging member 900 through threaded or gear toothed area 1320 cooperating with threaded arm 1000. Such a threaded or gear toothed connection can be referred to as a rack and pinion type connection. Additionally, as shown in FIG. 5 control screw 1500 can be operatively connected to adjusting screw or gear 1200 by means of threaded or gear toothed area 1260 of adjusting screw or gear 1200. Such a threaded or gear toothed connection can be referred to as a worm gear type connection.

Wedging members 700 and 900 can be slidably connected to body 210 of adjustable implant 200 through a series of pins and tracks. As shown in FIGS. 6 through 8 body or gear box 210 can be comprised of first end 250 and second end 252. Guide 500 can be connected to body 210 by first and second longitudinal arms 440 and 460. First end 250 can have a raised portion 370 and guide 500 on second end 252 can include a base 550. As shown in FIG. 8, raised portion 370 can include track 420 and track 430. Also as shown in FIG. 8 base 550 can include track 560 and track 570. Opposed tracks 420, 430, 560, and 570 can form a three dimensional track system for wedging members 700 and 900 to slide back and forth in (as schematically indicated in FIGS. 6, 7, 15, and 18.

Adjustment screw 1200 can be rotatively connected to body 210 through bore 270 in second end and bore 580 in guide 500. Tip 1220 can rotatively sit in bore 580 and head 1230 can rotatively sit in bore 270.

In one embodiment body 210 can include a cover for head 1230 which would prevent adjusting screw 1200 from coming out of body or gear box 210. Although not shown in another embodiment to prevent adjustment screw from falling out of body 210 wherein a threaded or gear toothed area 1260 can extend a length 1270 from top 1240 of head 1240 to a point before reaching the base 1250, after which point non-threaded area 1230 of head 1230 will be found. Control screw 1500 will threadably engage the threaded portion 1260 of adjustment screw 1100, but control screw 1500 will resist longitudinal movement of adjustment screw 1200 by threads 1530 contacting the non-threaded area 1230 of adjustment screw 1200 and not allowing longitudinal movement.

As shown in FIGS. 1, 2, 6-8, 11, 14, and 15, wedging members 700 and 900 can be constructed substantially identical. Wedging member 700 can be substantially identical to wedging member 900 but essentially rotated one hundred and eighty degrees so that the bottom 720 of wedging member 700 is in line with the top 910 of wedging member 900. Each of the wedging members 700, 900 can respectively be provided with a gear panel or arm 800, 1000 having a threaded or toothed rack 802, 1002. Wedging member 700 has gear panel or arm 800 with toothed rack 802. Wedging member or plate 900 has gear panel or arm 1000 with toothed rack 1002. Therefore, only the construction of wedging member 900 will be described in detail. Wedging member 900 can comprise top 910, bottom 920, interior portion 930, exterior portion 940, curved portion 950. Wedging member 900 can also include threaded or gear toothed arm 1000 and four rails or prongs 960, 970, 980, and 990.

Looking at FIGS. 6 through 8, and 15 through 18, it can be seen that wedging member 900 can be slidably connected to body 210 through its rails or prongs 960 and 970 slidably connecting to slots 570 and 560 of the base 550 of guide 500; and through its rails or prongs 990 and 980 slidably connecting to slots 430 and 420 of raised area 370. The four rails or prongs of wedging member 900 can maintain a straight path for wedging member sliding in the slots of raised area 370 of body 210, and base 550 of guide 500. Similarly the rails or four prongs of wedging member 700 can maintain a straight path for wedging member sliding in the slots of raised area 370 of body 210, and base 550 of guide 500. The extent of expansion and retraction of wedging members 700 and 900 can be controlled by threaded area 1310 cooperating with threaded arm 800 of wedging member 700, and threaded area 1320 cooperating with threaded arm 1000 of wedging member 900. In this manner wedging members 700 and 900 can be held in place at a selected amount of expansion or contraction (regardless of where they have been expanded or retracted to) as long as wedging members' 700 and 900 prongs remain at least partially sitting in the specified slots.

Each wedging member 700 or 900 can maintain a straight (generally vertical) path for wedging member 700, 900 sliding in the slots 420, 430, 560, and 570. The extent of expansion and retraction of wedging members/plates 700 and 900 can be controlled by screw/gear 1200. In this manner plates/wedging members 700 and 900 can be held in place at a selected amount of expansion or contraction (regardless of where they have been expanded or retracted to) as long as wedging members' 700 and 900 rails 760,770, 780, 790 (for wedging member 700) and rails 960,970, 980, and 990 (for wedging member 900) remain at least partially sitting in the specified slots.

To ensure that the prongs remain at least partially in the slots, the radial extent of threading for threaded areas 1310 and 1320 can be selected by having non-threaded areas 1330 and 1340. That is when the radial extent of the threaded area is reached, the specific wedging member (700 and/or 900) will stop its expansion. As shown in FIG. 4, a second safe guard can be provided in the amount of radial threading 1260 for the worm gear portion of adjusting screw 1200. In a preferred embodiment, an angular amount 1280 of about 120 degrees of radial threading 1260 can be provided which will restrict further rotation of screw 1200 when the threads angularly reach point 1262 or 1264 (see FIG. 5).

As shown in FIG. 8 arms 440 and 460 can include notches 450, 452, 470, and 472 to accommodate the rails or prongs of wedging members 700 and 900, and allow complete retraction of wedging members 700 and 900. Without these notches the prongs of wedging members 700 and 900 would prevent complete retraction.

Figure 11:
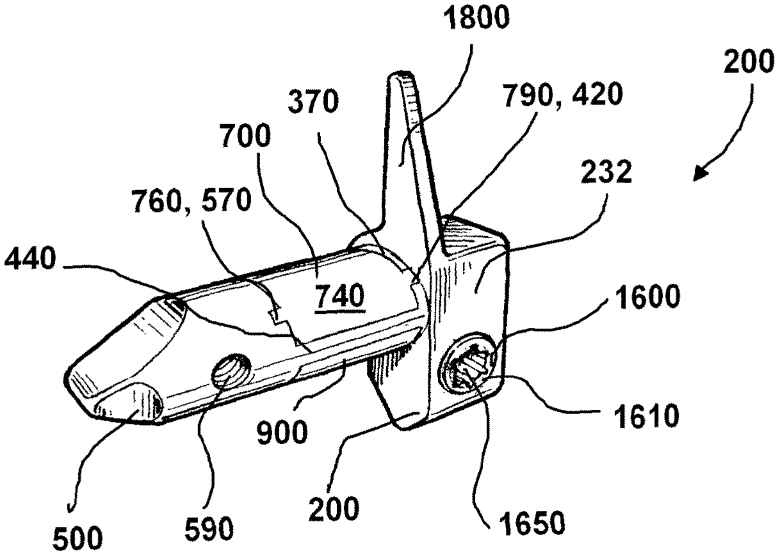
FIG. 11 is a partial perspective view of the preferred embodiment of the apparatus of the present invention.

FIG. 11 is a perspective view of adjustable implant 200 placed on its side. In this embodiment wedging members 700 and 900 are completely retracted and their exterior surfaces 740 and 940 are flush with raised area 370 of second end 230 and base 550 of guide 500. Making the exterior surfaces flush when wedging members 700 and 900 are fully retracted resists damage to bone and tissue during the initial insertion process (as no sharp edges are seen).

After the desired or proper expansion or retraction is obtained with wedging members 700 and 900, control screw 1500 can be locked in place by locking screw 1600. Locking screw 1600 can include first end 1610, second end 1620, and threaded area 1640. Locking screw 1600 can have bore 1650 which allows access to control screw 1500 even when locking screw 1600 is connected to the bore 330 for locking screw 1600. Bore 1650 allows locking screw to be in place even when adjusting control screw 1500. This feature reduces the amount of free parts the surgeon must keep track of during the operation (and prevents control screw 1500 and locking screw 1600 from falling out during an implantation procedure). In one embodiment a cover for bore 330 can be provided which prevents locking screw 1600 from being completely removed from body 210. After the desired amount of distraction is obtained, preferably, control screw 1500 is locked in place by second end 1620 of locking screw 1600 squeezing control screw 1500 against base 210 of bore 300. This squeezing frictionally locks in place control screw 1500. Even if not frictionally locked by locking screw 1600, the status of being a worm gear connection between control screw 1500 and threads 1260 of adjustment screw 1200, would tend to be self locking. However, without locking screw 1600, vibrations and other movements of implant 200 over time may tend to cause adjustment screw 1200 to rotate and cause unwanted movement of wedging members 700 and 900. Preferably, when locking screw 1600 is locked in place, first end 1610 is flush with top 232 of body 210.

Adjustable implant 200 and its components can be made of a number of materials, including but not limited to, stainless steel, titanium, ceramics, plastics, elastics, composite materials or any combination of the above. In addition, the modulus of elasticity of the implant can be matched to that of bone, so that the implant is not too rigid. The flexibility of the implant can further be enhanced by providing additional apertures or perforations throughout the implant.

Preferably, adjustable implant provides for distraction in the range of about 8 mm to about 11 mm in one embodiment (more preferably about 8 mm to about 10.7 mm), and in another embodiment in the rage of about 10 mm to about 15 mm (more preferably about 10.5 mm to about 14 mm).

In one embodiment an implantation guide 500 can be provided. Positioned at the other end of body 210 can be guide 500. Guide 500 can be triangularly shaped so as to be a pointed and arrow shaped guide. Alternatively, guide 500 can be in the shape of a cone with lateral truncated sides along the longitudinal axis wedging members 700 and 900. Guide 500 can include a threaded bore 590. In other embodiments guide 500 can be bulbous, cone shaped, pointed, arrow shaped, and the like, in order to assist in the insertion of adjustable implant 200 between adjacent spinous processes. Preferably, the insertion technique disturbs as little of the bone and surrounding tissue or ligaments as possible in order to (a) reduce trauma to the site and facilitate early healing, and (b) not destabilize the normal anatomy. In various embodiments there is no requirement to remove any of the bone of the spinous processes and depending on the anatomy of the patient, there may be no requirement to remove or sever ligaments and tissues immediately associated with the spinous processes.

In one embodiment guide 500 has a cross section which is adjacent to the cross section of completely retracted wedging members 700 and 900 and of similar shape. Where guide 500 and completely retracted wedging members 700 and 900 have elliptical cross sections, preferably the major dimension of guide's 500 cross section is about equal to the major dimension of completely retracted wedging members 700 and 900 cross section, and guide's 500 minor dimension about equal to completely retracted wedging members 700 and 900 cross section. In this embodiment, guide 500 can extend from body 210 of implant 200 with a cross section which reduces in size in a direction away from body 210. In another embodiment, guide 500 can be cone shaped with a base located adjacent wedging members 700 and 900. Further, in one embodiment guide 500 can have a base cross section about the same as an oval cross section of completely retracted wedging members 700 and 900.

In one embodiment guide 500 has faces 520 and 530 which are at about 45 degree angles (other angles, such as by way of example only, from about 30 degrees to about 60 degrees, and from about 25 to about 75 degrees are also envisioned), with a tip 540 so that adjustable implant 200 can be more easily urged between the spinous processes.

In one embodiment, adjustable implant can have a central body portion, the central body portion including wedging members 700 and 900, with a longitudinal axis 212. Extending from the central body portion can be a first wing 1800 and second wing 2000 which can be substantially perpendicular to longitudinal axis 212. Wings 1800 and 2000 can resist the tendency of adjustable implant to slide out from between spinous processes 100 and 110. In one embodiment second wing 2000 can detachably connectable to adjustable implant 200. In one embodiment second wing 2000 can be laterally adjustable relative to first wing 1800 to accommodate spinous processes of varying sizes and dimensions arrows 2002 and 2004 in FIG. 17 schematically indicate lateral adjustment of second wing 2000. Making wing 2000 detachably connectable facilitates insertion of adjustable implant between spinous processes 100 and 110, such as through guide 500.

In one embodiment, completely retracted wedging members 700 and 900 can have an elliptical cross section with a major axis which is substantially perpendicular to a major dimension (e.g., longitudinal axis) of first wing 1800 along longitudinal axis. Making these two axes substantially perpendicular facilitates proper positioning of adjustable implant 200 between selected spinous processes 100 and 110, and ensuring that substantial portions of wedging members 700 and 900 come in contact with both the upper and lower spinous processes so that the reaction loads can be more evenly distributed on the spinous processes by wedging members 700 and 900 during implantation and subsequent spinal column movements after implantation.

Wings 1800 and 2000 which are not perpendicular to longitudinal axis 212 are envisioned, and can be offset by 5, 10, 15, 20, and/or 25 degrees from the perpendicular and/or any range without such amounts. As shown in FIG. 3, first wing 1800 can include an upper area 1830 and a lower area 1840. Upper area can include a rounded end 1832. Rounded end 1832 can be designed to accommodate the anatomical form or contour various portions of the vertebrae, for example L4 (for a L4 L5 placement) or L5 (for a L5 S1 placement) superior lamina of the vertebra. It is to be understood that the same shape or variations of this shape can be used to accommodate other lamina of any vertebra. The lower portion 1842 can also be rounded in order to accommodate the vertebrae.

In one embodiment guide 500 can include a threaded bore 590 which accepts a screw 2130 in order to hold a second wing 2000 in position. With the second wing 2000 in position, the screw 2130 when it is positioned in the threaded bore 590 can engage and hold second wing 2000 in position relative to first wing 1800.

First and second wings 1800 and 2000 can come in a variety of shapes in order to provide for variations in the anatomical form of the spinous processes. Such shapes can be as depicted in FIGS. 103, 104, 105, 106, and 107 of U.S. Pat. No. 7,101,375. In these configurations, the wing has an upper portion and a lower portion. In FIG. 104, the lower portion is thicker than the upper portion in order to accommodate the spinous process, where the lower spinous process is thinner than the upper spinous process. In FIG. 105, both the upper and lower portions are enlarged over the upper and lower portions of FIG. 103 to accommodate both the upper and lower spinous processes being smaller. That is to say that the space between the upper and lower portions of the first and second wings are reduced due to the enlarged upper and lower portions of the second wing. Alternative embodiments of second wings 2000, as shown in FIGS. 104 and 105, are depicted in FIGS. 106 and 107. In these FIGS. 106 and 107, the second wing accommodates the same anatomical shape and size of the spinous processes as does the second wing in FIGS. 104 and 105 respectively. However, in the embodiments of the second wing of FIGS. 106 and 107, substantial masses have been removed from the wings. The upper and lower portions are essentially formed or bent in order to extend from the central portion of the second wing.

Figure 12:
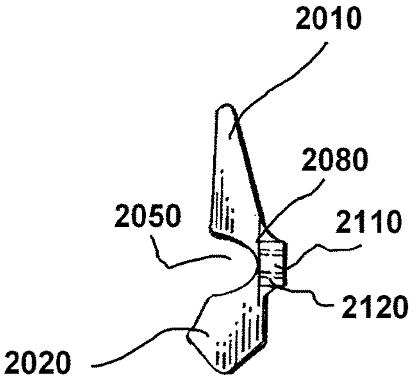
FIG. 12 is a fragmentary view showing second fixture or wing.
Figure 13:
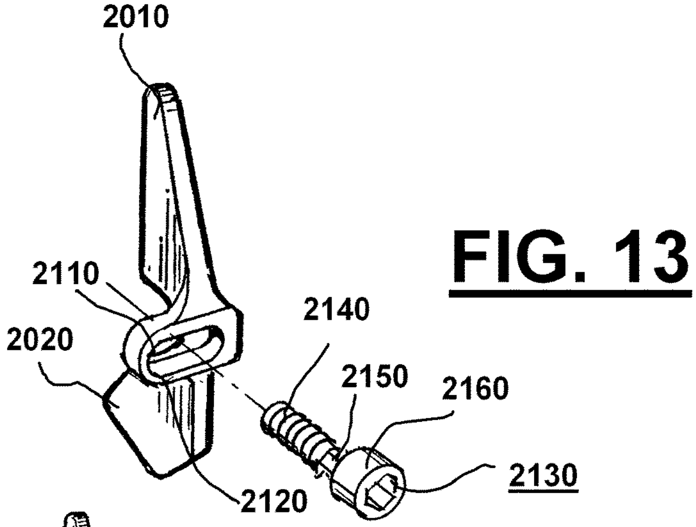
FIG. 13 is a fragmentary view of second fixture or wing.
Figure 14:
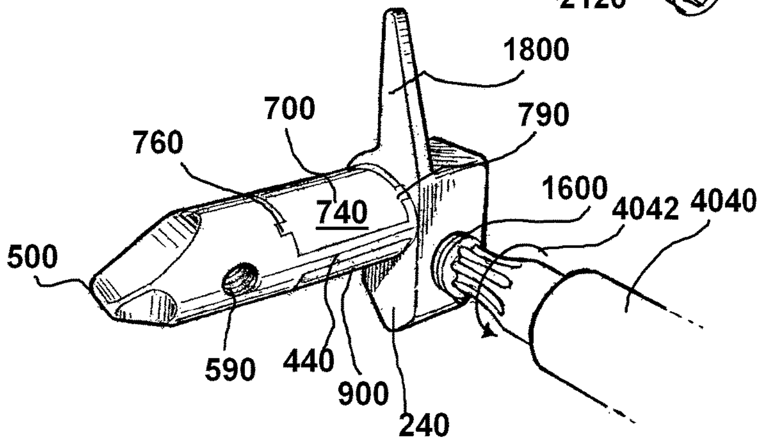
FIG. 14 is a partial perspective view of the preferred embodiment of the apparatus of the present invention.

FIGS. 12 and 13 are views of second wing 2000 and connecting screw 2130. Connecting screw 2130 can comprise threaded area 2140 and reduced cross sectional area 2150. Reduced cross sectional area 2150 can allow second wing member 2000 to slide (and be longitudinally adjustable) relative to screw 2130 (and first wing member 1800). Second wing member 2000 can include track 2110 and track can include threaded area 2120. Second wing member 2000 can include first end 2010, second end 2020, and cutout area 2050. Cutout area 2050 can be shaped to fit around the outer surface of guide 500. Alternatively, cutout area 2050 can be enlarged to allow full distraction of wedging members 700 and 900 (see e.g., FIG. 35 with second wing 2000 and cutout area 2050).

FIG. 15 is a perspective view of adjustable implant 200 having first and second wedging members 700 and 900 extended in the directions of arrows 702 and 902 and control screw 1500 being turned in the direction of arrow 4032, causing adjusting screw or gear 1200 to turn in the direction of arrow 214 along longitudinal centerline 212.

FIG. 17 is a perspective view of adjustable implant 200 placed in between spinous processes 110 and 120. Preferably a longitudinal line 2008 through second wing 2000 will be parallel to a longitudinal line 1808 going through first wing 1800. Arrows 2002 and 2004 schematically indicate the adjustability of second wing 2000 relative to first wing 1800 by varying the distance D.

FIG. 18 is a side perspective view of adjustable implant 200 showing a tool 4030 being used on the control screw 1500 to adjust adjusting screw 1500 and change the state of first 700 and second 900 wedging members. In FIG. 18 is shown both line 212 (which is the axis of rotation of adjusting screw or gear 1200) and a line 218 which is perpendicular to the axis of rotation of control screw 1500 (schematically indicated by arrow 4032). As shown in FIG. 1, line 218 can be spaced apart by the distance A from the axis of rotation of control screw 1500. As can be seen the axis of rotation of control screw 1500 does not intersect the axis of rotation of adjusting screw or gear 1200.

Adjustable implant 200 can be positioned adjacent to upper and lower vertebrae 120 and 130. Extending upwardly from vertebrae 120 and 130 are the upper and lower spinous processes 100 and 110. In a preferred embodiment, the fit of adjustable implant 200 between spinous processes 100 and 110 can be such that wings 1800 and 2000 do not touch spinous processes 100 and 110. One advantage of wings 1800 and 2000 is that they resist dislodgment of adjustable implant 200 from between spinous processes 100 and 110.

Preferably, during the surgical process first and second wedging members 700 and 900 of adjustable implant 200 are urged between spinous processes 100 and 110. After this has occurred, second wing 2000 can be guided by the other sides of the spinous processes from a path which causes the plane of second wing 2000 to move substantially parallel to the plane of first wing 1800 until screw 2130 can be placed in threaded bore 590 of guide 500. Bolt 2130 can be tightened to secure second wing 2000.

In one embodiment a second wing 2000 is not used where it was deemed impractical or unnecessary to use a second wing 2000.

In one embodiment neither a first 1800 nor a second 2000 wing is used where the anatomy between the spinous processes 100 and 110 was such that it would be undesirable to use either a first or second wing.

In one embodiment the spinous processes 100 and 110 can be accessed and distracted initially using appropriate instrumentation, and adjustable implant 200 can be inserted and adjusted in order to maintain and achieve the desired distraction. In another embodiment the spinous process can be accessed and adjustable implant 200 appropriately positioned. Once positioned, implant 200 can be expanded in order to distract the spinous processes or extend the distraction of already distracted spinous processes. Accordingly, adjustable implant 200 can be used to create or increase a previously created distraction, or to maintain a distraction which has already been created.

FIGS. 19-23 show an instrument or tool 5000 that can be used to rotate either the control screw 1500 and/or the locking screw/nut 1600 and adjust adjustable implant 200. Tool 5000 can include body 5010, shaft 5014, control screw head 5020, locking screw head 5030, driver 5120, driver 5130, counter torque handle 5200, base 5300, and set prongs 5310, 5320. Torque handle 5200 can be connected to body 5010 and enables a surgeon to hold and support the tool/instrument 5000. Driver 5130 can be slidingly and rotatively connected to body 5010. Driver 5130 can include locking screw head 5030. Driver 5120 can be slidingly and rotatively connected to driver 5130. Driver 5120 can include control screw head 5020. Driver 5130 can be connected to shaft 5134 which itself is connected to locking screw head 5030. Base 5300 can be connected to body 5010 and include two set prongs 5310 and 5320. Set prongs 5310 and 5320 can locate or set tool 5000 relative to body 210 of adjustable implant 200 by matching set prongs 5310 and 5320 with openings 5310 and 5320. Once set the individual drivers 5120 and 5130 can be used to drive control screw head 5020 and locking screw head 5030 which respectively will turn control screw 1500 and locking screw 1600. Arrows 5121 and 5122 schematically indicate slidable movement of driver 5120. Arrow 5017 schematically indicates rotation of driver 5120 (which can also be in the opposite direction). Arrows 5015 and 5016 schematically indicate slidable movement of driver 5130. Arrow 5017 schematically indicates rotation of driver 5130 (which can also be in the opposite direction). Tool 5000 is a preferred tool in that it allows both control screw 1500 and locking screw 1600 to be manipulated with a single instrument. Additionally, it can optionally have a placement system (body 5300 and prongs 5310 and 5320). Body 5300 can be a distal flange or bracket that carries one or more projections or prongs 5310 and 5320. If the optional body 5300 is employed, the gear case or body 210 carries sockets 5310 and 5320 that are sized and shaped correspondingly to projections 5310 and 5320. In this fashion, the surgeon can interlock the projections 5310 and 5320 with the sockets 5310 and 5320' to help rigidify the connection of the tool or instrument 5000 to the body or gear case 210 when an adjustment of either of the screws 1500 or 1600 is required.

FIGS. 24-27 show another embodiment of the apparatus of the present invention, designated by the numeral 200A. The embodiment of FIGS. 24-27 is basically the same as the embodiment of FIGS. 1-23. However, the first and second fixtures or wings 1800, 2000 are respectively provided with prongs or projections or spikes 1872, 1882 which enhance gripping of the spine 30 (and spinous processes 100 and 110).

Figure 28:
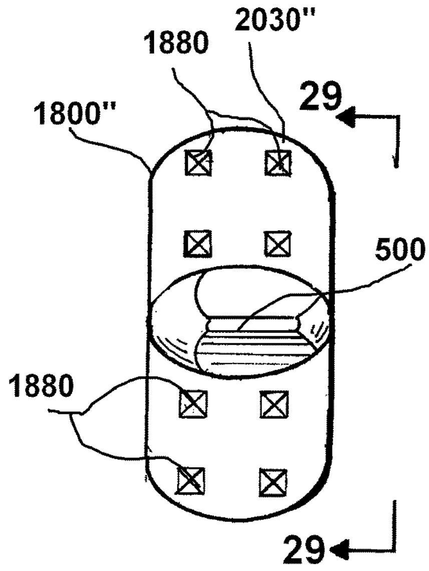
FIG. 28 is a side view of a third embodiment of the apparatus of the present invention.
Figure 29:
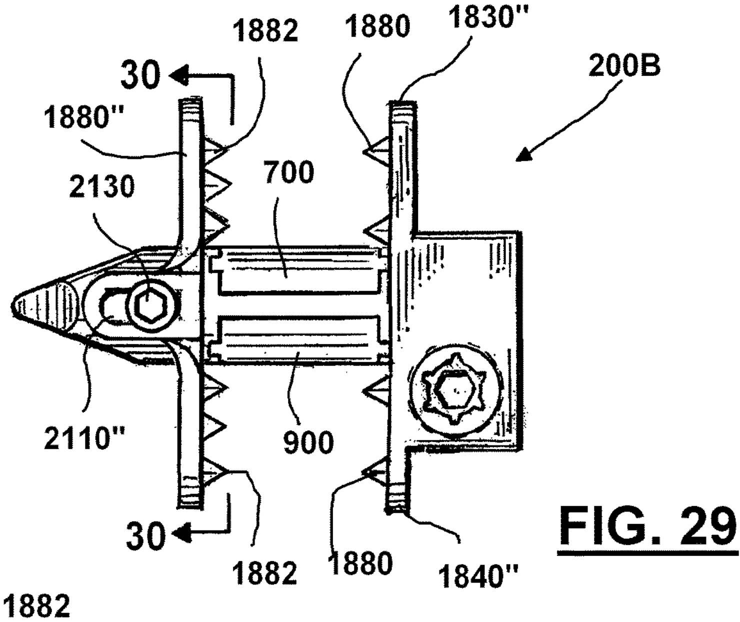
FIG. 29 is a view taken along lines 29-29 of FIG. 28.
Figure 30:
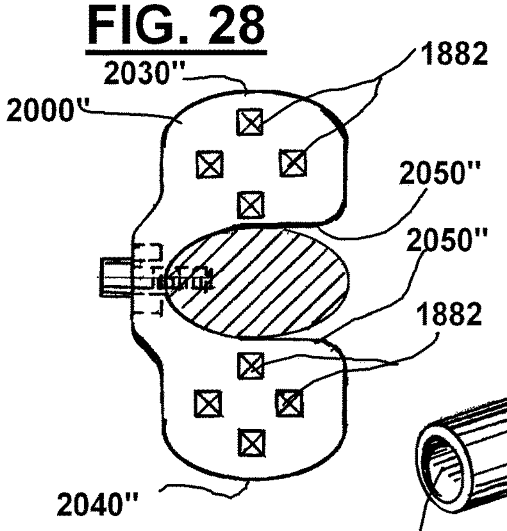
FIG. 30 is a view taken along lines 30-30 of FIG. 29.

FIGS. 28-30 show another embodiment of the apparatus of the present invention, designated generally by the numeral 200B. In FIGS. 28-30, the implant 200B is similar in construction to the embodiment of FIGS. 1-23 with the exception of the shape of the wings 1800, 2000 being generally rectangular, but also providing rounded or curved end portions. The first wing 1800 provides upper and lower rounded or curved end portions 1830, 1840. The second wing or fixture 2000 provides upper and lower rounded or curved end portions 2030, 2040. As with the preferred embodiment, the second fixture or wing 2000" provides a concavity 2050 that is receptive of body 210. As with the preferred embodiment, a fastener 2130 enables attachment of second fixture or wing 2000 to body 210 using fastener 2130 with a track/slot 2110 as with the embodiment shown in FIG. 13. In one embodiment concavity 2050 can be expanded to allow wedging members 700 and 900 to be fully distracted even where second wing 2000 is placed over wedging members 700 and 900.

Figure 31:
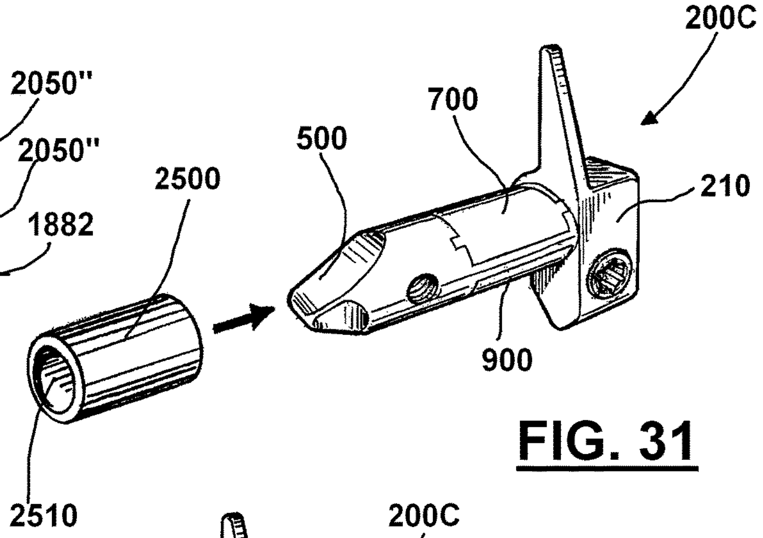
FIG. 31 is a perspective view of a fourth embodiment of the apparatus of the present invention.
Figure 32:
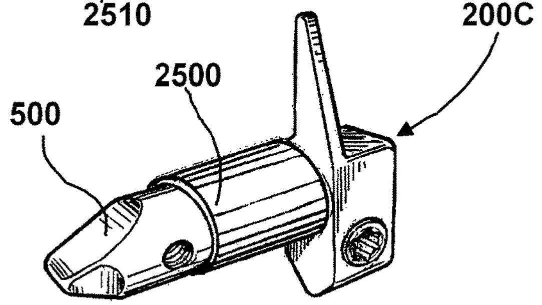
FIG. 32 is a perspective view of a fourth embodiment of the apparatus of the present invention.
Figure 33:
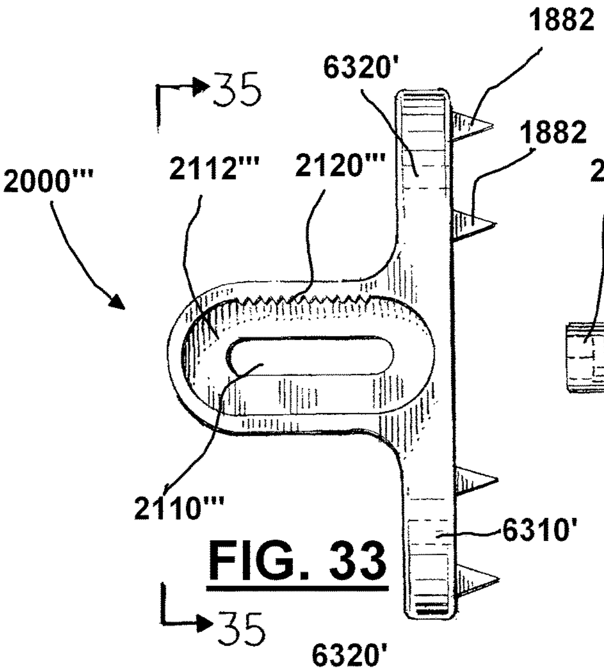
FIG. 33 is a top view of an alternative embodiment of a second wing which is laterally adjustable relative to the first wing.
Figure 34:
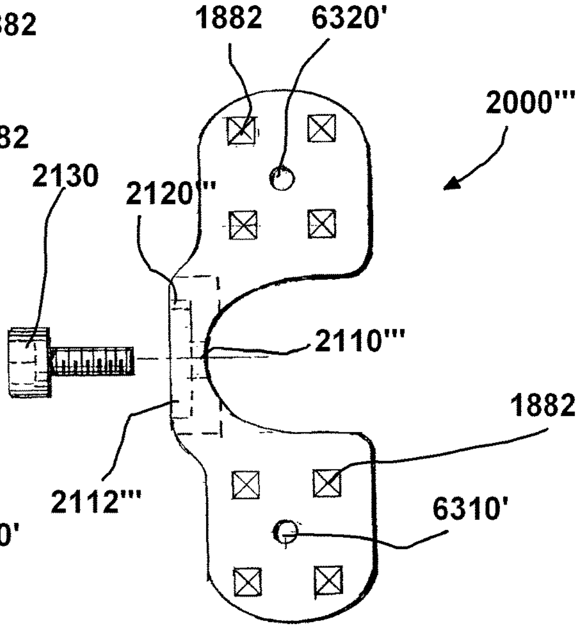
FIG. 34 is a side view of the wing of FIG. 33.
Figure 35:
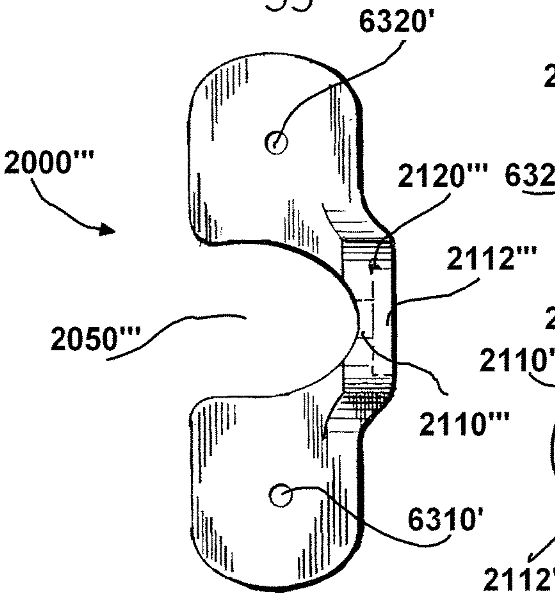
FIG. 35 is a side view of the wing of FIG. 33 taken from the lines 35-35.
Figure 36:
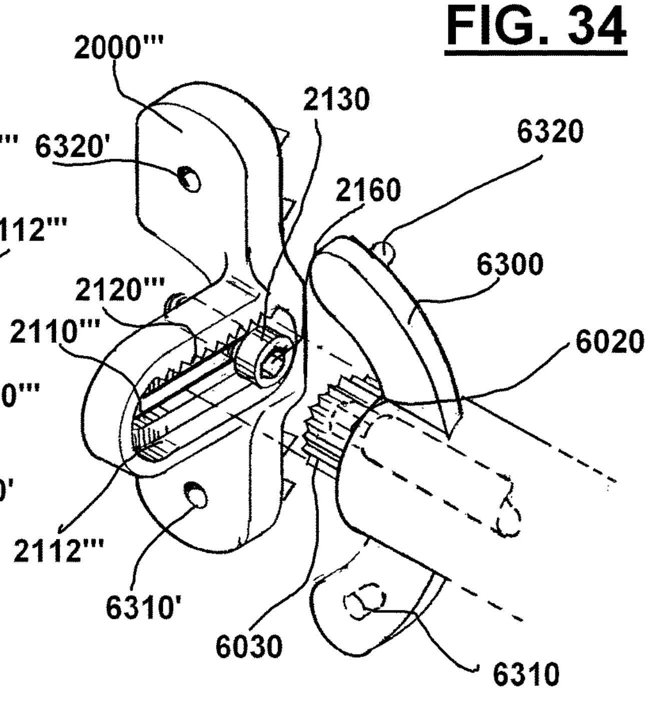
FIG. 36 is a perspective view showing wing adjustment tool being connected to the second wing of FIG. 33.
Figure 41:
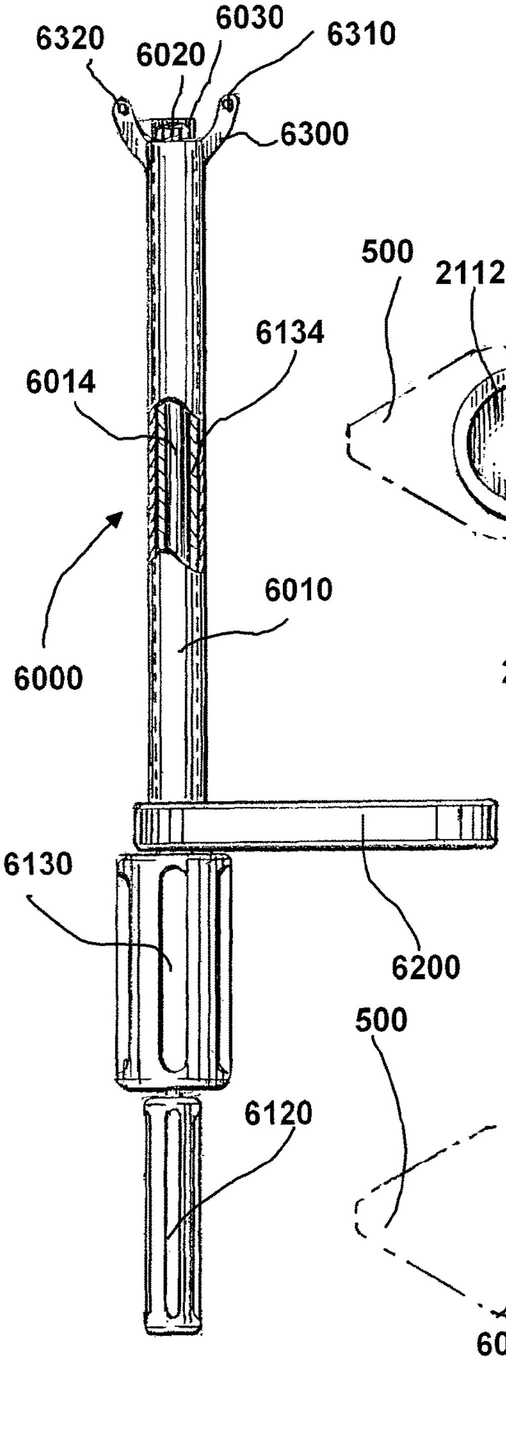
FIG. 41 is a partial sectional view of the wing adjustment tool of FIG. 37.
Figure 42:
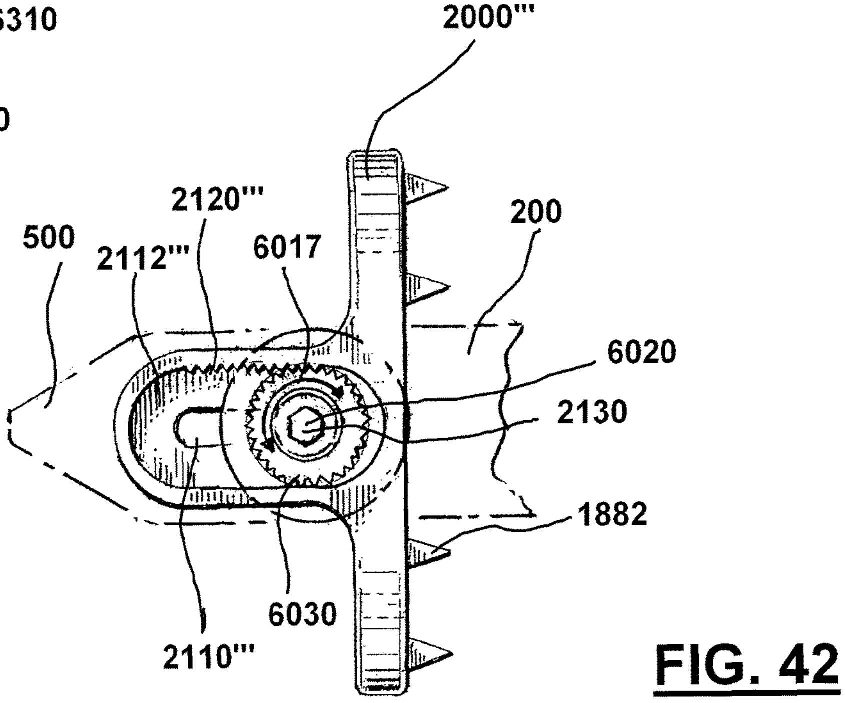
FIG. 42 is a top view of the wing adjustment tool of FIG. 37 connected to the second wing of FIG. 33.
Figure 43:
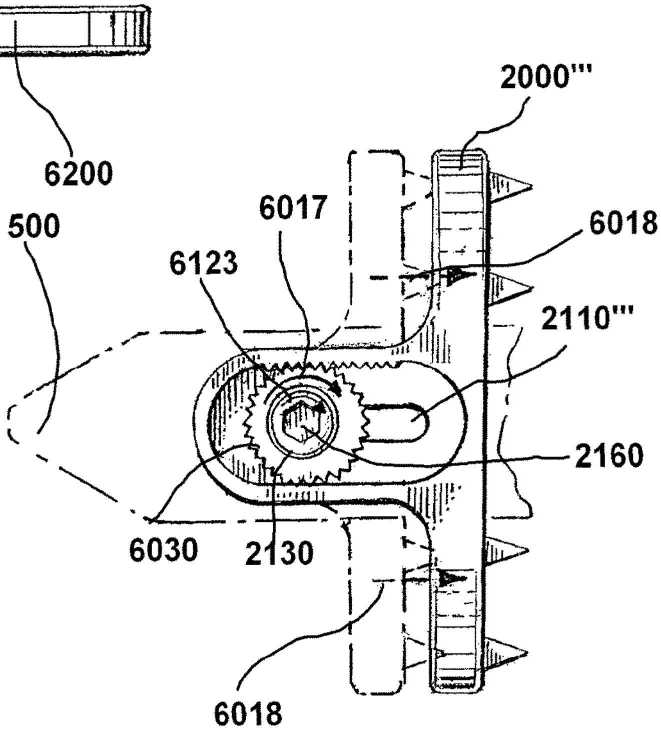
FIG. 43 shows the second wing being laterally adjusted.

FIGS. 31-32 show yet another embodiment, designated generally by the numeral 200C. Adjustable implant 200C provides the same basic construction of the embodiment of FIGS. 1-18 with the addition of a flexible sleeve 2500 that is placed over the body 210 (and wedging members 700 and 900) as shown in FIGS. 31 and 32. The sleeve 2500 has a hollow bore or open ended cavity 2510 that enables the sleeve 2500 to occupy a position on body 210, basically covering wedging members 700 an 900, when the wedging members/plates 700 and 900 are expanded or retracted, the sleeve acts as an interface or cushion in between the wedging members 700 and 900 and the surrounding tissue. This can prevent pinching, tearing, or damage to the surrounding tissue.

FIGS. 33 through 43 show one embodiment for laterally adjusting the second wing relative to the first wing with another embodiment of second wing 2000. FIGS. 36-43 show an instrument or tool 6000 that can be used to slidingly adjust/clamp second wing 2000 relative to first wing 1800 of various adjustable implants. Tool 6000 can include body 6010, shaft 6014, wing fastener screw head 6020, sliding adjuster screw head 6030, driver 6120, driver 6130, counter torque handle 6200, base 6300, and set prongs 6310, 6320. Torque handle 6200 can be connected to body 6010 and enables a surgeon to hold and support the tool/instrument 6000. Driver 6130 can be slidingly and rotatively connected to body 6010. Driver 6130 can include sliding adjuster screw head 6030. Driver 6120 can be slidingly and rotatively connected to driver 6130. Driver 6120 can include fastener screw head 6020. Base 6300 can be connected to body 6010 and include two set prongs 6310 and 6320. Set prongs 6310 and 6320 can locate or set tool 6000 relative to second wing 2000 of adjustable implant 200 by matching set prongs 6310 and 6320 with openings 6310 and 6320. Once set the individual driver 6130 can be used to slidingly adjust second wing 2000 relative to first wing (for a clamping effect) of adjustable implant 200. When the proper adjustment between the two wings is achieved, driver 6120 can be used to lock fastener 2130 with control screw head 6020. By adjusting second wing 2000 closer to the other wing (in a clamping motion), the two wings can grab hold of and/or bite into spinous processes 100 and 110 to resist relative movement between the adjustable implant and the spinous processes. Arrow 6017 schematically indicates rotation of driver 6130. Arrows 6018 schematically indicate movement of second wing 2000 in a clamping motion (relative to first wing 1800 which is not shown). Body 6300 can be a distal flange or bracket that carries one or more projections or prongs 6310 and 6320. If the optional body 6300 is employed, the second wing 2000 carries sockets 6310 and 6320 that are sized and shaped correspondingly to projections 6310 and 6320. In this fashion, the surgeon can interlock the projections 6310 and 6320 with the sockets 6310 and 6320 to help rigidify the connection of the tool or instrument 6000 to the second wing 2000 before adjustment of second wing relative to the adjustable implant to obtain a clamping motion. After head 6030 is inside of well 2112 and attached to gear teeth or threads 2120 second wing 2000 will slide along adjustable implant via opening 2050 sliding over adjustable implant. In one embodiment the amount of adjustment of second wing 2000 is limited so that this wing does not travel over wedge members 700 and/or 900. Projections or prongs 1882 help stabilize adjustable implant relative to the spinal processes. In one embodiment opening 2050 can be enlarged to allow full expansion/distraction of wedging members 700 and 900 even where second wing 2000 is adjusted over wedging members 700 and 900.

Various alternative embodiments or options for any of the above described will be described below.

In one embodiment adjustable implant 200 can act as an extension stop. For example, adjustable implant can resist or stop further extension between spinous processes 100 and 110 once the back has been bent backwardly such that adjustable implant 200 stops further movement of adjacent spinous processes 100 and 110 towards each other. The distance between wedging members 700 and 900 can stop movement spinous processes 100 and 110 toward each other. Adjustable implant 200 does not limit the flexion of spinal column 30 (because in flexion spinal column 30 is bent forwardly and spinous processes 100 and 110 move away from each other (and away from wedging members 700 and 900).

In one embodiment only one wedging member 700 is provided. In this embodiment wedging member 900 can be permanently attached to body 210 (and arm 100 either removed entirely or the threading removed). In this embodiment wedging member can expand or retract based on movement of adjustment screw 1200. In this embodiment about one half of the adjusting expansion or distraction capability will be available compared to embodiment where two wedging members 700 and 900 are provided.

In one embodiment only one longitudinal arm 440 is provided. The shape of wedging members 700 and 900 can be adjusted to compensate for forming an elliptical cross section when completely retracted.

Although not shown, in one embodiment only one adjustable wedging member or plate 700 (or 900) is provided. In this embodiment it is expected that only one half of the adjustability of a two wedge/plate member will be provided.

Although not shown, in one embodiment a cap can be placed over first longitudinal bore 270 which also will prevent adjusting screw 1200 from leaving first longitudinal bore 270. This cap can also prevent adjustable implant 200 from being disassembled after manufacture which can prevent improper reassembly. This cap can be laser welded to body 210. In one embodiment one or more timing marks can be placed on adjusting screw 1200 (e.g., its head 1230) and body 210 which marks can show proper alignment of adjusting screw 1200 relative to body 210 (ensuring proper installation of the components).

Although not shown, in one embodiment one or more raised areas or detents can be included on first wing 1800 which can limit the expansion of wedging members 700 and/or 900. These raised areas or detents can act as an additional factor of safety beyond the various amounts of threading on adjusting screw 1200 (middle section 1300 and head 1230).

In one embodiment wedging members 700 and 900 have a flat, irregular, or concave shape.

Surgical Method

With all the ligaments (such as the superspinous ligament) and tissues associated with the spinous processes left intact, adjustable implant 200 can be implanted essentially floating in position in order to gain the benefits of extension stop and not limiting flexion. In one embodiment the spinous processes can be accessed and distracted initially using appropriate instrumentation, and adjustable implant 200 can be inserted and adjusted in order to maintain and achieve the desired distraction. In another embodiment the spinous process can be accessed and adjustable implant 200 appropriately positioned. Once positioned, implant 200 can be expanded in order to distract the spinous processes or extend the distraction of already distracted spinous processes. Accordingly, adjustable implant 200 can be used to create or increase a previously created distraction, or to maintain a distraction which has already been created.

Ideally, adjustable implant 200 would be placed close to the instantaneous axis of rotation of spinal column 30 so that the reaction forces adjustable implant places on spinal column 30 are minimized.

For purposes of surgical implantation of adjustable implant 200 into a patient, the patient is preferably positioned on his side and placed in a flexed (tucked) position in order to distract the upper and lower vertebrae.

In a preferred procedure, a small incision is made on the midline of the spinous processes. The spinous processes are spread apart or distracted with a spreader. The incision is spread downwardly toward the table, and adjustable implant 200 is preferably inserted upwardly between the spinous processes 100 and 110 in a manner that maintains the distraction of spinous processes. The adjustable implant 200 is urged upwardly until guide 500 and at least part of wedging member 700 and/or 900 are visible on the other side of the spinous process. Once this is visible, the incision is spread upwardly away from the table and the retaining unit or second wing 2000 can be attached via screw 2130. Track 2110 can be used to space second wing 2000 relative to first wing 1800 (at least to the extent of allowable movement through slot 2110). After this had occurred, the incisions can be closed.

An alternative surgical approach requires that small incisions be made on either side of the space located between the spinous processes. The spinous processes are spread apart or distracted using a spreader placed through the upper incision. From the lower incision, adjustable implant 200 can be inserted upwardly between spinous processes 100 and 110 in a manner that urges the spinous processes apart. Adjustable implant 200 can be urged upwardly until guide 500 and at least part of wedging member 700 and/or 900 are visible through the second small incision in the patient's back. Once this is visible, second wing 2000 can be attached to guide 500 through screw 2130. After this has occurred, the incisions can be closed.

The advantage of the above two surgical procedures is that a surgeon is able to observe the entire operation, where he can look directly down onto the spinous processes as opposed to having to view the procedure from positions which are to the right and to the left of the spinous processes. Generally, the incision is as small as possible and the surgeon is working in a bloody and slippery environment. Thus, an implant that can be positioned directly in front of a surgeon is easier to insert and assemble than an implant which requires the surgeon to shift from side to side. Accordingly, a top down approach, as an approach along a position to anterior line is preferred so that all aspects of the implantation procedure are fully visible to the surgeon at all times. This aides in the efficient location of (i) the adjustable implant 200 between the spinous processes, (ii) the retaining second wing 2000 in adjustable implant 200, and (iii) finally screw 2130 in adjustable implant 200.

In one embodiment the method can include implanting adjustable implant 200 between two spinous processes 100 and 110, expanding adjustable implant 200 a first amount, allowing spine 30 to creep or adjust to this first amount of distraction, and then expanding adjustable implant 200 a second amount, and then allowing a period of time spine 30 to creep or adjust to this new level of distraction. This process could be repeated until the desired amount of overall distraction has been accomplished. This stepped wise (and wait) distraction method can be used with insertion tools prior to the installation of adjustable implant 200. The tools can be used to obtain the desired distraction using a series of spinal distraction and spinal creep periods before firs implanting adjustable implant 200.

One embodiment uses a dilator tool 4010 and a distractor tool 4020. The patient can be placed prone or lateral. A skin incision can be made over spinous processes 100 and 110 where the stenosis exists. The muscle will be moved off of the spinous process to the base bilaterally. If the facet joint is too large, the top can be removed to facilitate placement of adjustable implant 200 at the base of spinous process 110. The inter spinous ligament is left intact. A small dilator 4010 can be placed through the inter spinous ligament near the base. A second distracter 4020 is then used to open the space up to accommodate the smaller adjustable implant 200. Adjustable implant is then adjusted causing wedging members 700 and 900 to expand a desired amount in the direction of arrows 702 and 902. Adjustment is obtained by rotation of a control screw 1500 which rotates an adjustment screw or worm gear 1200. During this expansion process the surgeon can feel the inter spinous ligament. Once taught, adjustable implant 200 can be allowed to sit and settle for a period of time (such as for five minutes). After this settling period of time, control screw 1500 can be tightened a bit more causing wedging members 700 and 900 to expand a bit more and ensure that the inter spinous ligament remains taught. If adjustable implant 200 cannot be expanded to a point where there is the desired amount of stretching of the inter spinous ligament, then a larger sized adjustable implant 200 can be used and adjusted accordingly. Adjustable implant allows the attachment of a second wing 2000 to prevent lateral dislodgment of adjustable implant from spinous processes 100 and 110. Preferably, the area is irrigated with antibiotics and saline and the muscle is injected with local anesthetic and the wound is closed.

FIGS. 16 through 18 show various steps in one embodiment of the method of implanting adjustable implant 200. FIG. 16 is a perspective view of a portion of a spinal column 30 where adjustable implant 200 is being inserted between a first spinous process 100 and a second spinous process 110 (guide 500 facilitates such insertion). FIG. 17 shows adjustable implant 200 being more fully inserted between a first spinous process 100 and a second spinous process 110 and second wing 2000 being attached. FIG. 18 shows adjustable implant 200 after first 700 and second 900 wedging members have been extended more fully (in the directions of arrows 702 and 902) pushing apart first spinous process 100 and second spinous process 110.

INDUSTRIAL APPLICABILITY

From the above, it is evident that the embodiments can be used to relieve pain caused by spinal stenosis in the form of such as that caused by central canal stenosis or foraminal (lateral) stenosis. Various embodiments have the ability to flatten the natural curvature of the spine and open the neural foramen and the spacing between adjacent vertebra to relieve problems associated with the above mentioned lateral and central stenosis. Additionally, various embodiments can be used to relieve pain associated with facet arthropathy. Various embodiment can be implanted with surgery that is minimally invasive and can be used on an outpatient basis.

The following is a list of reference numerals:

LIST FOR REFERENCE NUMERALS

| (Part No.) Reference Numeral | (Description) Description |
|---|---|
| 10 | patient |
| 20 | back |
| 30 | spinal column |
| 40 | vertebrae |
| 50 | vertebra |
| 60 | nerves |
| 70 | blood vessels |
| 100 | first spinous process |
| 110 | second spinous process |
| 120 | upper vertebra |
| 122 | arrow |
| 130 | lower vertebra |
| 132 | arrow |
| 200 | implant |
| 202 | arrow |
| 210 | body |
| 212 | longitudinal axis |
| 214 | arrow |
| 215 | arrow |
| 216 | plane |
| 218 | line |
| 220 | first end |
| 230 | second end |
| 232 | top |
| 240 | housing |
| 250 | first end of housing |
| 252 | second end of housing |
| 260 | width of first end |
| 270 | first longitudinal bore |
| 280 | base |
| 290 | second longitudinal bore |
| 300 | control screw bore |
| 310 | base of control screw bore |
| 320 | opening between control screw bore and first longitudinal bore |
| 330 | locking screw bore |
| 340 | threaded area |
| 350 | base of locking screw bore |
| 360 | second end of housing |
| 370 | raised portion |
| 380 | first side of raised portion |
| 390 | shape |
| 400 | second side of raised portion |
| 410 | shape |
| 420 | first track |
| 430 | second track |
| 440 | first longitudinal arm |
| 450 | notch |
| 452 | notch |
| 460 | second longitudinal arm |
| 470 | notch |
| 472 | notch |
| 500 | insertion guide |
| 510 | arrow head |
| 520 | first face |
| 530 | second face |
| 540 | tip |
| 550 | base |
| 560 | first track |
| 570 | second track |
| 580 | longitudinal bore |
| 590 | threaded bore for second wing |
| 600 | distracting unit |
| 610 | central body |
| 620 | spacer |
| 630 | cross section |
| 640 | ellipse |
| 650 | major axis |
| 660 | minor axis |
| 670 | longitudinal axis |
| 700 | first wedging member |
| 702 | arrow |
| 710 | top |
| 720 | bottom |
| 730 | interior portion |
| 740 | exterior portion |
| 742 | outermost point of exterior |
| 750 | curved portion |
| 760 | first prong |

-continued

LIST FOR REFERENCE NUMERALS

| (Part No.) Reference Numeral | (Description) Description |
|---|---|
| 770 | second prong |
| 780 | third prong |
| 790 | fourth prong |
| 800 | threaded arm |
| 802 | geared or toothed area |
| 810 | tip of threaded arm |
| 820 | shape of tip |
| 830 | length of threaded arm |
| 900 | second wedging member |
| 902 | arrow |
| 910 | top |
| 920 | bottom |
| 930 | interior portion |
| 940 | exterior portion |
| 942 | outermost point of exterior |
| 950 | curved portion |
| 960 | first prong |
| 970 | second prong |
| 980 | third prong |
| 990 | fourth prong |
| 1000 | threaded arm |
| 1002 | geared or toothed area |
| 1010 | tip of threaded arm |
| 1020 | shape of tip |
| 1030 | length of threaded arm |
| 1200 | adjusting screw or worm gear |
| 1210 | first end |
| 1220 | second end |
| 1230 | head |
| 1240 | top of head |
| 1250 | base of head |
| 1260 | threaded area |
| 1262 | end of threaded area |
| 1264 | end of threaded area |
| 1270 | length of threads from top to base of head |
| 1280 | angular extent of threaded area |
| 1300 | middle section |
| 1310 | first threaded area |
| 1320 | second threaded area |
| 1330 | first non-threaded area |
| 1340 | second non-threaded area |
| 1360 | tip |
| 1500 | control screw |
| 1510 | first end |
| 1520 | second end |
| 1530 | threaded area |
| 1540 | receiving area for adjusting tool |
| 1550 | arrow |
| 1554 | arrow |
| 1556 | arrow |
| 1558 | arrow |
| 1600 | locking screw |
| 1610 | first end |
| 1620 | second end |
| 1630 | reduced area of second end or tip |
| 1640 | threaded area |
| 1650 | receiving area for adjusting tool |
| 1800 | first wing |
| 1830 | upper area |
| 1832 | rounded area |
| 1840 | lower area |
| 1842 | rounded area |
| 1872 | plurality of spikes or proj ections |
| 1882 | plurality of spikes or projections |
| 2000 | second wing |
| 2002 | arrow |
| 2004 | arrow |
| 2010 | first end |
| 2020 | second end |
| 2030 | upper area |
| 2040 | lower area |
| 2050 | cutout area |
| 2060 | first side |
| 2070 | second side |

-continued

LIST FOR REFERENCE NUMERALS

| (Part No.) Reference Numeral | (Description) Description |
|---|---|
| 2080 | middle section |
| 2090 | base of middle section |
| 2100 | curved area of base |
| 2110 | track |
| 2120 | threaded area |
| 2130 | connecting screw |
| 2140 | threaded area |
| 2150 | reduced cross sectional area |
| 2160 | receiving area for adjusting tool |
| 2500 | flexible sleeve member |
| 2510 | opening or bore |
| 3000 | first distraction amount |
| 3010 | second distraction amount |
| 3020 | extension stop |
| 4000 | instrumentation |
| 4010 | dilator tool |
| 4020 | distractor tool. |
| 4030 | adjusting tool |
| 4032 | arrow |
| 4040 | adjusting tool |
| 4042 | arrow |
| 5000 | tool |
| 5010 | body |
| 5014 | shaft |
| 5015 | arrow |
| 5016 | arrow |
| 5017 | arrow |
| 5020 | control screw head |
| 5030 | locking screw head |
| 5120 | driver |
| 5121 | arrow |
| 5122 | arrow |
| 5123 | arrow |
| 5130 | driver |
| 5134 | body |
| 5200 | counter torque handle |
| 5300 | base |
| 5310 | set prong |
| 5320 | set prong |
| 6000 | tool |
| 6010 | body |
| 6014 | shaft |
| 6015 | arrow |
| 6016 | arrow |
| 6017 | arrow |
| 6018 | arrows |
| 6020 | locking screw head |
| 6030 | adjustable rack screw head |
| 6120 | driver |
| 6121 | arrow |
| 6122 | arrow |
| 6123 | arrow |
| 6130 | driver |
| 6200 | counter torque handle |
| 6300 | base |
| 6310 | set prong |
| 6320 | set prong |

All measurements disclosed herein are at standard temperature and pressure, at sea level on Earth, unless indicated otherwise. All materials used or intended to be used in a human being are biocompatible, unless indicated otherwise.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

We claim:

1. An implant positionable between a first spinous process and a second spinous process of a spinal column, the implant comprising:

a central body configured to be inserted between the first spinous process and the second spinous process, the central body comprising:

a housing, and an elongated member extending from the housing, the elongated member having a longitudinal axis;

a first wing fixed relative to the central body; and a second wing removably coupled to the elongated member and adjustable along the elongated member, wherein the second wing defines a cutout area configured to receive the elongated member in a transverse direction and the second wing extends only partially about the elongated member;

a threaded fastener extending through the second wing and configured to engage the elongated member to selectively secure the second wing in a desired position, wherein the threaded fastener is threadingly movable between a tightened position configured to maintain the second wing in the desired position and a loosened position configured to enable movement of the second wing relative to the elongated member without threading movement of the threaded fastener;

an adjustment mechanism at least partially located in the housing;

first and second wedging members disposed at least partially within the elongated member and controllable by the adjustment mechanism;

wherein the adjustment mechanism comprises two interfacing geared members operatively coupled to the first and second wedging members such that movement of the at least two interfacing geared members controls expansion and retraction of the first and second wedging members relative to the elongated member in a direction perpendicular to the longitudinal axis to increase or decrease the amount of distraction between the first and second spinous processes.

2. The implant of claim 1, wherein the elongated member of the central body comprises a cone-shaped insertion guide with lateral truncated sides configured to assist in the insertion of the implant between the first spinous process and the second spinous process.

3. The implant of claim 1, wherein the elongated member of the central body comprises a pointed and arrow-shaped insertion guide configured to assist in the insertion of the implant between the first spinous process and the second spinous process.

4. The implant of claim 3, wherein the insertion guide comprises a tip, a first face extending from the tip, and a second face extending from the tip and angled relative to the first face between 25 degrees and 75 degrees.

5. The implant of claim 3, wherein the insertion guide comprises a tip, a first face extending from the tip, and a second face extending from the tip angled relative to the first face at about 45 degrees.

6. The implant of claim 1, wherein the first wing includes a first portion and a second portion and both the first portion and the second portion extend from the central body substantially perpendicular to, and offset from, the longitudinal axis.

7. The implant of claim 1, wherein the second wing comprises a first portion extending from the central body substantially perpendicular to the longitudinal axis, a second portion extending from the central body substantially perpendicular to the longitudinal axis, and a middle section, wherein the first portion, second portion, and middle section define the cutout area.

8. The implant of claim 7, wherein at least one of the first portion and the second portion of the second wing is offset relative to the longitudinal axis.

9. The implant of claim 7, wherein the middle section of the second wing comprises a track defining an elongated slot configured to receive the threaded fastener.

10. The implant of claim 9, wherein the second wing is movable parallel along the elongated member at a distance defined by the engagement of the threaded fastener and elongated slot.

11. The implant of claim 1, wherein one of the two interfacing geared members has a threaded portion operably connected to the first wedging member and a non-threaded portion which limits the amount of expansion to the first wedging member.

12. The implant of claim 1, wherein the cutout area is configured to allow the first and second wedging members to move to a position of full distraction when the second wing is coupled to the elongated member.

13. An implant positionable between a first spinous process and a second spinous process of the spinal column, the implant comprising:

a central body configured to be inserted between the first spinous process and the second spinous process, the central body comprising:

a housing having at least a portion of an adjustment mechanism provided therein, the adjustment member including two interfacing geared members, and an elongated member extending from the housing, the elongated member having a longitudinal axis;

a first wedging member disposed at least partially within the elongated member and controllable by the adjustment mechanism, the first wedging member able to linearly expand and retract relative to the elongated member in a direction perpendicular to the longitudinal axis in order to increase or decrease the amount of distraction between the first and second spinous processes;

a first wing extending from the central body substantially perpendicular to the longitudinal axis; and a second wing removably coupleable to the elongated member in a direction perpendicular to the longitudinal axis and defining a cutout to receive the elongated member and allow the first wedging member to be positioned in a fully distracted position when the second wing is coupled to the elongated member;

a threaded fastener extending through the second wing and configured to engage the elongated member to selectively secure the second wing in a desired position, wherein the threaded fastener is threadingly movable between a tightened position configured to maintain the second wing in the desired position and a loosened position configured to enable movement of the second wing relative to the elongated member without threading movement of the threaded fastener.

14. The implant of claim 13, wherein the first wedging member is substantially flush with an exterior surface of the central body when the first wedging member is in a retracted position.

15. The implant of claim 14, further comprising a second wedging member disposed at least partially within the elongated member and controllable by the adjustment mechanism, the second wedging member able to linearly expand and retract relative to the elongated member in a direction perpendicular to the longitudinal axis and opposite the first wedging member to increase or decrease the amount of distraction between the first and second spinous processes.

16. The implant of claim 15, wherein the second wedging member is substantially flush with an exterior surface of the central body when the second wedging member is in a retracted position.

17. An implant positionable between a first spinal body and a second spinal body, the implant comprising:

a central body comprising:

a housing;

an adjustment mechanism at least partially located within the housing and including two interfacing geared members;

an elongated member extending from the housing; and first and second wedging members at least partially disposed within the elongated member and controllable by the adjustment mechanism to increases or decrease an amount of distraction between the first and second spinal bodies;

a first wing fixedly coupled to the central body; and a second wing removably coupled to the elongated member of the central body and adjustable along a length of the elongated member, the second wing enabling full distraction of the first and second wedging members when the second wing is coupled to the elongated member;

a threaded fastener extending through the second wing and configured to engage the elongated member to selectively secure the second wing in a desired position, wherein the threaded fastener is threadingly movable between a tightened position configured to maintain the second wing in the desired position and a loosened position configured to enable movement of the second wing relative to the elongated member without threading movement of the threaded fastener.

* * * * *